US012692318B2

(12) United States Patent
Li et al.

(10) Patent No.: US 12,692,318 B2
(45) Date of Patent: Jul. 28, 2026

(54) ANTI-4-1BB NANOBODIES

(71) Applicant: LANOVA MEDICINES LIMITED, Shanghai (CN)

(72) Inventors: Runsheng Li, Shanghai (CN); Wentao Huang, Shanghai (CN)

(73) Assignee: LANOVA MEDICINES LIMITED, Shanghai (CN)

( * ) Notice: Subject to any disclaimer, the term of this patent is extended or adjusted under 35 U.S.C. 154(b) by 0 days.

(21) Appl. No.: 19/197,775

(22) Filed: May 2, 2025

(65) Prior Publication Data

US 2025/0320307 A1     Oct. 16, 2025

Related U.S. Application Data

(63) Continuation of application No. 18/687,277, filed as application No. PCT/CN2022/115536 on Aug. 29, 2022.

(30) Foreign Application Priority Data

Aug. 31, 2021     (WO) ............... PCT/CN2021/115621

(51) Int. Cl.
*C07K 16/28*          (2006.01)
(52) U.S. Cl.
CPC ...... *C07K 16/2878* (2013.01); *C07K 2317/24* (2013.01); *C07K 2317/31* (2013.01); *C07K 2317/565* (2013.01); *C07K 2317/569* (2013.01)
(58) Field of Classification Search
None
See application file for complete search history.

(56) References Cited

U.S. PATENT DOCUMENTS

| | | | | |
|---|---|---|---|---|
| 10,501,551 B2 * | 12/2019 | Eckelman | ............... | A61P 35/00 |
| 2018/0021440 A1 | 1/2018 | Yu et al. | | |
| 2018/0258177 A1 | 9/2018 | Kwon et al. | | |
| 2020/0362051 A1 | 11/2020 | Brucklacher-Waldert et al. | | |
| 2020/0377595 A1 | 12/2020 | Shimizu et al. | | |
| 2021/0253724 A1 * | 8/2021 | Claus | .................... | C07K 16/40 |
| 2024/0209106 A1 | 6/2024 | Qu et al. | | |

FOREIGN PATENT DOCUMENTS

| | | |
|---|---|---|
| CN | 108659131 A | 10/2018 |
| CN | 110627906 A | 12/2019 |
| CN | 112646031 A | 4/2021 |
| WO | 2010001251 A2 | 1/2010 |
| WO | 2016165302 A1 | 10/2016 |
| WO | 2017123650 A2 | 7/2017 |

(Continued)

OTHER PUBLICATIONS

Wang et al., Single-domain antibodies as therapeutics for solid tumor treatment, Acta Pharmaceutica Sinica B, 14(7):2854-2868, 2024.*

(Continued)

*Primary Examiner* — Claire Kaufman
(74) *Attorney, Agent, or Firm* — Sheppard, Mullin, Richter & Hampton LLP

(57)          ABSTRACT

Provided are anti-4-1BB nanobodies and bispecific or multispecific antibodies that incorporate the nanobodies. Methods of using the antibodies for treating and diagnosing diseases such as cancer are also provided.

6 Claims, 10 Drawing Sheets

Specification includes a Sequence Listing.

(56)                References Cited

FOREIGN PATENT DOCUMENTS

WO        2019141268  A1      7/2019
WO        2022242679  A1      11/2022
WO        2023030258  A1      3/2023

OTHER PUBLICATIONS

International Search Report for PCT International Application No. PCT/CN2024/078991, dated Jun. 3, 2024, 6 pages.
Written Opinion of the International Searching Authority for PCT International Application No. PCT/CN2024/078991, dated Jun. 3, 2024, 4 pages.
Decary, S. et al. "Preclinical Activity of SAR408701: A Novel Anti-CEACAM5-maytansinoid Antibody-drug Conjugate for the Treatment of CEACAM5-positive Epithelial Tumors" Clinical Cancer Research, vol. 26, No. 24, Dec. 15, 2020 (Dec. 15, 2020), pp. 6589-6599.

Muik, A. et al. "Preclinical Characterization and Phase I Trial Results of a Bispecific Antibody Targeting PD-L1 and 4-1BB (GEN1046) in Patients with Advanced Refractory Solid Tumors" Cancer Discovery, Feb. 17, 2022 (Feb. 17, 2022), pp. 1248-1265.
Powell et al. A functional genomic screen in vivo identifies CEACAM5 as a clinically relevant driver of breast cancer metastasis. npj, Breast Cancer, 2018; 4(9):1-12. (Year: 2018).
Zhai, T. et al. "Generation of a safe and efficacious llama single-domain (vHH) targeting the membranproximal region of 4-1BB for engineering therapeutic bispecific antibodies for cancer" Journal for Immuno Therapy of Cancer, vol. 9, No. 6, Jun. 30, 2021.
International Search Report and Written Opinion dated Nov. 29, 2022 for International Patent Application No. PCT/CN2022/115536, 11 pages.
Chabrol Eric et al: "VHH characterization. Recombinant VHHs: Production, characterization and affinity", Analytical Biochemistry, Academic Press, Amsterdam, NL, vol. 589, Oct. 30, 2019 (Oct. 30, 2019).

* cited by examiner

ANTI-4-1BB NANOBODIES

CROSS REFERENCE TO RELATED APPLICATIONS

The present application is a continuation of U.S. patent application Ser. No. 18/687,277, filed Feb. 27, 2024, which is a U.S. National Stage Application under 35 U.S.C. 371 of International Patent Application No. PCT/CN2022/115536, filed Aug. 29, 2022, which claims priority to International Patent Application No. PCT/CN2021/115621, filed Aug. 31, 2021, the content of each of which is incorporated herein by reference in its entirety in the present disclosure.

SEQUENCE LISTING

The instant application contains a Sequence Listing which has been submitted in XML format via Patent Center and is hereby incorporated by reference in its entirety. Said XML copy, created Feb. 27, 2024, is named 70LG-340200-US_Sequence Listing and is 58,914 bytes in size.

BACKGROUND 4-1BB (CD137, tumor necrosis factor receptor superfamily 9) is a member of TNF-receptor superfamily (TNFRSF) and is a costimulatory molecule which is expressed following the activation of immune cells, both innate and adaptive immune cells. 4-1BB plays an important role in modulating the activity of various immune cells. 4-1BB agonists enhance immune cell proliferation, survival, secretion of cytokines and cytolytic activity CD8 T cells. Many other studies showed that activation of 4-1BB enhances immune response to eliminate tumors in mice. Therefore, it was suggested that 4-1BB is a promising target molecule in cancer immunology.

A single-domain antibody (sdAb), also known as a nanobody, is an antibody fragment consisting of a single monomeric variable antibody domain. Nanobodies produced from camelids and certain other animals are also referred to as VHH fragments. Like a whole antibody, a nanobody is able to bind selectively to a specific antigen. With a molecular weight of only 12-15 kDa, single domain antibodies are much smaller than common antibodies (150-160 kDa). Single domain antibodies, given their small sizes and one-chain nature, can be particularly suitable for inclusion as a fragment in other proteins, such as chimeric antigen receptors (CAR) and bispecific antibodies.

SUMMARY

Provided are anti-human 4-1BB nanobodies which are suitable for inclusion in bispecific or trispecific antibodies. Accordingly, in one embodiment of the present disclosure, provided is a single domain antibody or a polypeptide comprising the single domain antibody, wherein the single domain antibody has binding specificity to the human 4-1BB protein and comprises a complementarity determining region 1 (CDR1), a CDR2 and a CDR3, wherein the CDR1, CDR2 and CDR3 comprise, respectively, the amino acid sequences of (a) the amino acid sequences of SEQ ID NO:18, 58 and 32; (b) the amino acid sequences of SEQ ID NO: 18, 59 and 38; (c) the amino acid sequences of SEQ ID NO:17, 24 and 31; (d) the amino acid sequences of SEQ ID NO:18, 25 and 32; (e) the amino acid sequences of SEQ ID NO:18, 26 and 33; (f) the amino acid sequences of SEQ ID NO:18, 27 and 34; (g) the amino acid sequences of SEQ ID NO:18, 28 and 35; (h) the amino acid sequences of SEQ ID NO: 19, 28 and 35; (i) the amino acid sequences of SEQ ID NO:20, 28 and 35; (j) the amino acid sequences of SEQ ID NO:19, 28 and 35; (k) the amino acid sequences of SEQ ID NO:21, 29 and 36; (l) the amino acid sequences of SEQ ID NO:22, 29 and 36; (m) the amino acid sequences of SEQ ID NO:21, 29 and 36; (n) the amino acid sequences of SEQ ID NO:21, 29 and 36; (o) the amino acid sequences of SEQ ID NO: 19, 26 and 33; (p) the amino acid sequences of SEQ ID NO:18, 28 and 37; (q) the amino acid sequences of SEQ ID NO:23, 30 and 38; or (r) the amino acid sequences of SEQ ID NO:18, 28 and 39.

In some embodiments, the CDR1 comprises the amino acid sequence of SEQ ID NO: 18, the CDR2 comprises the amino acid sequence of SEQ ID NO:58, and the CDR3 comprises the amino acid sequence of SEQ ID NO:32. In some embodiments, the single domain antibody or a polypeptide comprises the amino acid sequence of any one of SEQ ID NO: 40-48 and 60-62.

In some embodiments, the CDR1 comprises the amino acid sequence of SEQ ID NO: 18, the CDR2 comprises the amino acid sequence of SEQ ID NO:59, and the CDR3 comprises the amino acid sequence of SEQ ID NO:38. In some embodiments, the single domain antibody or a polypeptide comprises the amino acid sequence of any one of SEQ ID NO: 49-57.

In some embodiments, the single domain antibody or a polypeptide comprises the amino acid sequence of any one of SEQ ID NO:1-16.

Also provided is a composition comprising the antibody or the polypeptide and a pharmaceutically acceptable carrier. Still also provided is one or more polynucleotide encoding the antibody or the polypeptide, an isolated cell comprising one or more polynucleotide encoding the antibody or fragment thereof.

Treatment methods and uses are also provided. In one embodiment, a method of treating cancer in a patient in need thereof is provided, comprising administering to the patient an effective amount of the antibody or the polypeptide of the present disclosure. In some embodiments, the cancer is a solid tumor. In some embodiments, the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer. In some embodiments, the method further comprises administering to the patient a second cancer therapeutic agent.

DETAILED DESCRIPTION

Definitions

Figure 1A:
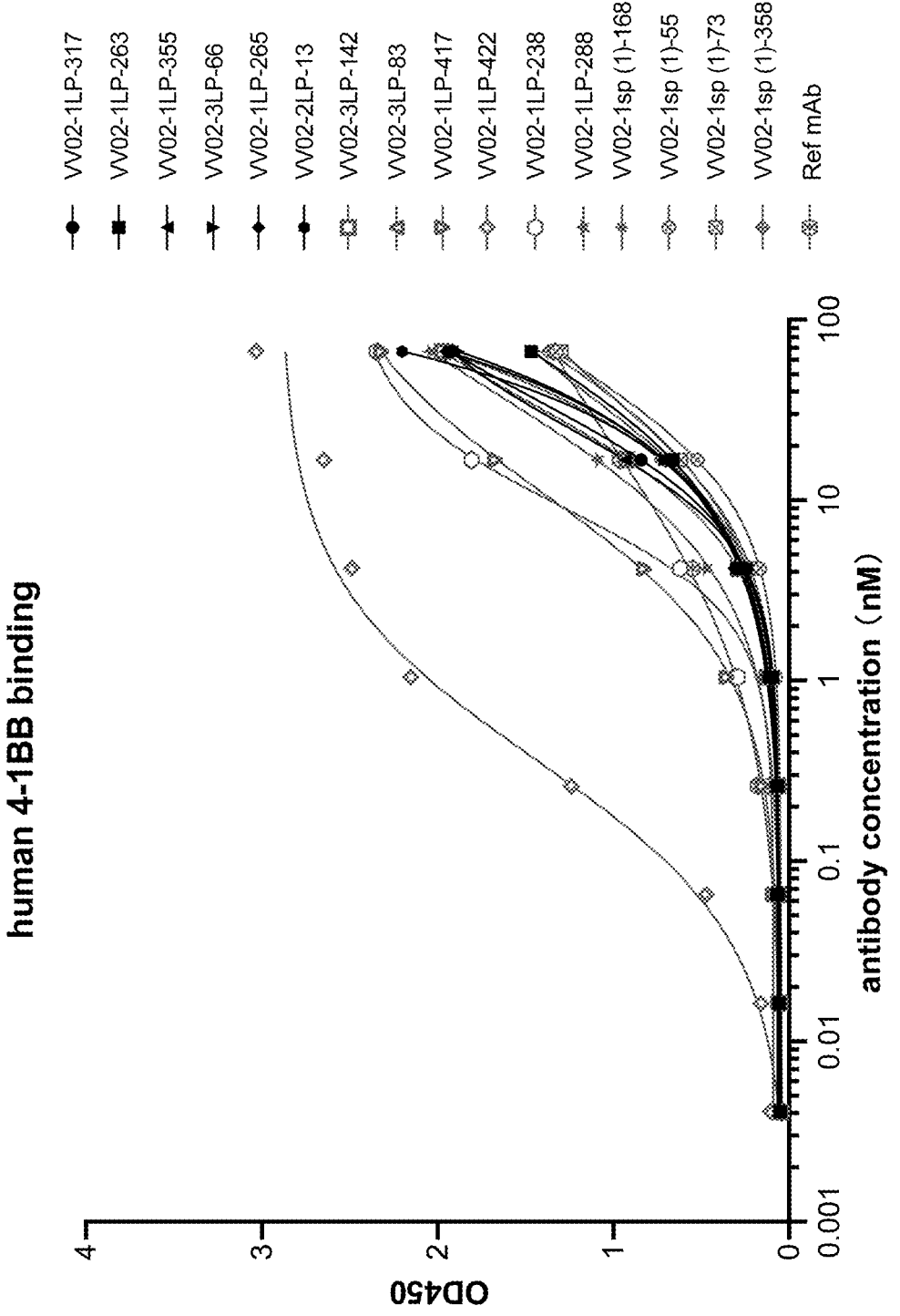
FIG. 1A-B show that the anti-41BB nanobodies dose-dependently bound to soluble human and cynomolgus 4-1BB.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody"

includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\varepsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-4-1BB Nanobodies

The present disclosure provides nanobodies, including humanized ones, against the human 4-1BB protein. These antibodies have high binding affinity to 4-1BB and can effectively block the interaction between 4-1BB and its ligand. As demonstrated in Example 4, these antibodies exhibited potent ability to induce 4-1BB-mediated NF-κB activity only in the presence of Fc crosslinking. Therefore, these antibodies are non-agonist antibodies which do not activate 4-1BB signaling on their own. When combined with a second antibody, however, the ensuing bispecific antibody can activate 4-1BB signaling in the presence of the target antigen of the second antibody. In other words, the present nanobodies are particularly suitable for development into bispecific or multi-specific antibodies.

Accordingly, in one embodiment of the present disclosure, provided is a single domain antibody or a polypeptide comprising the single domain antibody, wherein the single domain antibody includes a CDR1, a CDR2 and a CDR3, which respectively have the CDR1, CDR2 and CDR3 sequences of any one of the antibodies in Table 1.

In some embodiments, the CDR1, CDR2, and CDR3 are those of antibody VV02-1LP-317 (SEQ ID NO:1). In some embodiments, the CDR1, CDR2 and CDR3 include the amino acid sequences of SEQ ID NO: 17, 24 and 31, respectively. In some embodiments, the antibody includes the recited CDR1, CDR2 and CDR3 and has at least 80%, 85%, 90%, 95%, 98%, or 99% sequence identity to SEQ ID NO:1.

In some embodiments, the CDR1, CDR2, and CDR3 are those of antibody VV02-1LP-263 (SEQ ID NO:2). In some embodiments, the CDR1, CDR2 and CDR3 include the amino acid sequences of SEQ ID NO:18, 25 and 32, respectively. In some embodiments, the antibody includes the recited CDR1, CDR2 and CDR3 and has at least 80%, 85%, 90%, 95%, 98%, or 99% sequence identity to SEQ ID NO:2.

In some embodiments, the CDR1, CDR2, and CDR3 are those of antibody VV02-1LP-355 (SEQ ID NO:3). In some embodiments, the CDR1, CDR2 and CDR3 include the amino acid sequences of SEQ ID NO:18, 26 and 33, respectively. In some embodiments, the antibody includes the recited CDR1, CDR2 and CDR3 and has at least 80%, 85%, 90%, 95%, 98%, or 99% sequence identity to SEQ ID NO:3.

In some embodiments, the CDR1, CDR2, and CDR3 are those of antibody VV02-3LP-66 (SEQ ID NO:4). In some embodiments, the CDR1, CDR2 and CDR3 include the amino acid sequences of SEQ ID NO: 18, 27 and 34, respectively. In some embodiments, the 98%, or 99% sequence identity to SEQ ID NO:4.

In some embodiments, the CDR1, CDR2, and CDR3 are those of antibody VV02-1LP-265 (SEQ ID NO:5). In some embodiments, the CDR1, CDR2 and CDR3 include the amino acid sequences of SEQ ID NO: 18, 28 and 35, respectively. In some embodiments, the antibody includes the recited CDR1, CDR2 and CDR3 and has at least 80%, 85%, 90%, 95%, 98%, or 99% sequence identity to SEQ ID NO:5.

In some embodiments, the CDR1, CDR2, and CDR3 are those of antibody VV02-2LP-13 (SEQ ID NO:6). In some embodiments, the CDR1, CDR2 and CDR3 include the amino acid sequences of SEQ ID NO: 19, 28 and 35, respectively. In some embodiments, the antibody includes the recited CDR1, CDR2 and CDR3 and has at least 80%, 85%, 90%, 95%, 98%, or 99% sequence identity to SEQ ID NO:6.

In some embodiments, the CDR1, CDR2, and CDR3 are those of antibody VV02-3LP-142 (SEQ ID NO:7). In some embodiments, the CDR1, CDR2 and CDR3 include the amino acid sequences of SEQ ID NO:20, 28 and 35, respectively. In some embodiments, the antibody includes the recited CDR1, CDR2 and CDR3 and has at least 80%, 85%, 90%, 95%, 98%, or 99% sequence identity to SEQ ID NO:7.

In some embodiments, the CDR1, CDR2, and CDR3 are those of antibody VV02-3LP-83 (SEQ ID NO:8). In some embodiments, the CDR1, CDR2 and CDR3 include the amino acid sequences of SEQ ID NO:19, 28 and 35, respectively. In some embodiments, the antibody includes the recited CDR1, CDR2 and CDR3 and has at least 80%, 85%, 90%, 95%, 98%, or 99% sequence identity to SEQ ID NO:8.

In some embodiments, the CDR1, CDR2, and CDR3 are those of antibody VV02-1LP-417 (SEQ ID NO:9). In some embodiments, the CDR1, CDR2 and CDR3 include the amino acid sequences of SEQ ID NO:21, 29 and 36, respectively. In some embodiments, the antibody includes the recited CDR1, CDR2 and CDR3 and has at least 80%, 85%, 90%, 95%, 98%, or 99% sequence identity to SEQ ID NO:9.

In some embodiments, the CDR1, CDR2, and CDR3 are those of antibody VV02-1LP-422 (SEQ ID NO:10). In some embodiments, the CDR1, CDR2 and CDR3 include the amino acid sequences of SEQ ID NO:22, 29 and 36, respectively. In some embodiments, the 98%, or 99% sequence identity to SEQ ID NO:10.

In some embodiments, the CDR1, CDR2, and CDR3 are those of antibody VV02-1LP-238 (SEQ ID NO:11). In some embodiments, the CDR1, CDR2 and CDR3 include the amino acid sequences of SEQ ID NO:21, 29 and 36, respectively. In some embodiments, the antibody includes the recited CDR1, CDR2 and CDR3 and has at least 80%, 85%, 90%, 95%, 98%, or 99% sequence identity to SEQ ID NO:11.

In some embodiments, the CDR1, CDR2, and CDR3 are those of antibody VV02-1LP-288 (SEQ ID NO:12). In some embodiments, the CDR1, CDR2 and CDR3 include the amino acid sequences of SEQ ID NO:21, 29 and 36, respectively. In some embodiments, the antibody includes the recited CDR1, CDR2 and CDR3 and has at least 80%, 85%, 90%, 95%, 98%, or 99% sequence identity to SEQ ID NO:12.

In some embodiments, the CDR1, CDR2, and CDR3 are those of antibody VV02-1SP (1)-168 (SEQ ID NO:13). In some embodiments, the CDR1, CDR2 and CDR3 include the amino acid sequences of SEQ ID NO: 19, 26 and 33, respectively. In some embodiments, the antibody includes the recited CDR1, CDR2 and CDR3 and has at least 80%, 85%, 90%, 95%, 98%, or 99% sequence identity to SEQ ID NO:13.

In some embodiments, the CDR1, CDR2, and CDR3 are those of antibody VV02-1SP (1)-55 (SEQ ID NO:14). In some embodiments, the CDR1, CDR2 and CDR3 include the amino acid sequences of SEQ ID NO: 18, 28 and 37, respectively. In some embodiments, the antibody includes the recited CDR1, CDR2 and CDR3 and has at least 80%, 85%, 90%, 95%, 98%, or 99% sequence identity to SEQ ID NO: 14.

In some embodiments, the CDR1, CDR2, and CDR3 are those of antibody VV02-1SP (1)-73 (SEQ ID NO:15). In some embodiments, the CDR1, CDR2 and CDR3 include the amino acid sequences of SEQ ID NO:23, 30 and 38, respectively. In some embodiments, the antibody includes the recited CDR1, CDR2 and CDR3 and has at least 80%, 85%, 90%, 95%, 98%, or 99% sequence identity to SEQ ID NO:15.

In some embodiments, the CDR1, CDR2, and CDR3 are those of antibody VV02-1SP (1)-358 (SEQ ID NO:16). In some embodiments, the CDR1, CDR2 and CDR3 include the amino acid sequences of SEQ ID NO:18, 28 and 39, respectively. In some embodiments, the 98%, or 99% sequence identity to SEQ ID NO:16.

Humanized antibodies are also provided, such as those provided in SEQ ID NO:40-48 and 60-62 for antibody VV02-1LP-263 and SEQ ID NO:49-57 for antibody VV02-1SP (1)-73. For VV02-1LP-263 (CDR1 in SEQ ID NO:18, CDR2 in SEQ ID NO:25 and CDR3 in SEQ ID NO:32), the CDR2 can incorporate either or both of the mutations (D54G and D61E, Kabat numbering). Accordingly, in some embodiments, the CDR1, CDR2 and CDR3 include the amino acid sequences of SEQ ID NO:18, 58 and 32, respectively. In some embodiments, the antibody includes any one of SEQ ID NO:40-48 and 60-62. In some embodiments, the antibody includes the recited CDR1, CDR2 and CDR3 and has at least 80%, 85%, 90%, 95%, 98%, or 99% sequence identity to any one of SEQ ID NO:40-48 or 60-62.

Among these humanized sequences, 263 huNb-1-3_1 (SEQ ID NO:60), 263 huNb-1-3_2 (SEQ ID NO:61), and 263 hnNb-1-3_3 (SEQ ID NO:62) were further optimized ones, which were demonstrated (Example 7 and FIG. 6-7) to be suitable for further clinical development. In some embodiments, the antibody includes SEQ ID NO:60. In some embodiments, the antibody includes the recited CDR1, CDR2 and CDR3 and has at least 80%, 85%, 90%, 95%, 98%, or 99% sequence identity to SEQ ID NO:60. In some embodiments, the antibody includes SEQ ID NO:61. In some embodiments, the antibody includes the recited CDR1, CDR2 and CDR3 and has at least 80%, 85%, 90%, 95%, 98%, or 99% sequence identity to SEQ ID NO:61. In some embodiments, the antibody includes SEQ ID NO: 62. In some embodiments, the antibody includes the recited CDR1, CDR2 and CDR3 and has at least 80%, 85%, 90%, 95%, 98%, or 99% sequence identity to SEQ ID NO:62.

For VV02-1SP (1)-73 (CDR1 in SEQ ID NO:23, CDR2 in SEQ ID NO:30 and CDR3 in SEQ ID NO:38), a mutation (N31S, Kabat numbering) or either of two mutations (D54S and D61E, Kabat numbering) can be incorporated to the CDR1 and CDR2, respectively. Accordingly, in some embodiments, the CDR1, CDR2 and CDR3 include the amino acid sequences of SEQ ID NO: 18, 59 and 38, respectively. In some embodiments, the antibody includes any one of SEQ ID NO:49-57. In some embodiments, the antibody includes the recited CDR1, CDR2 and CDR3 and has at least 80%, 85%, 90%, 95%, 98%, or 99% sequence identity to any one of SEQ ID NO:49-57.

Also provided, in some embodiments, is an nanobody or polypeptide that includes the nanobody, which includes a CDR1 having an amino acid sequence selected from SEQ ID NO: 17-23, a CDR2 having an amino acid sequence selected from SEQ ID NO:24-30 or 58-59, and a CDR3 having an amino acid sequence selected from SEQ ID NO:31-39.

Also provided, in some embodiments, is an nanobody or polypeptide that includes the nanobody, which includes a CDR1 having an amino acid sequence selected from SEQ ID NO: 21-22, a CDR2 having the amino acid sequence of SEQ ID NO:29, and a CDR3 having the amino acid sequence of SEQ ID NO:36.

Also provided, in some embodiments, are anti-4-1BB antibodies and antigen binding fragments that compete with any of the antibodies disclosed herein in binding to human 4-1BB. Also provided, in some embodiments, are anti-4-1BB antibodies and antigen binding fragments that bind to the same epitope as any of the antibodies disclosed herein. Also provided, in some embodiments, are anti-4-1BB antibodies and antigen binding fragments that included the CDR1, CDR2, and CDR3 of the antibodies disclosed herein.

Also provided are compositions that include the antibody or the polypeptide and a pharmaceutically acceptable carrier.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence. In some embodiments, the modified antibody or fragment retains the designate CDR sequences.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Also provided are bispecific and multispecific antibodies that includes one, two, three or four units of the single domain anti-4-1BB antibody as disclosed herein, and one or more other specificities (not 4-1BB).

Bispecific and Multispecific Antibodies, and Chimeric Antigen Receptors (CAR)

As provided, the anti-4-1BB antibodies disclosed here are particularly useful for preparing bispecific and multispecific antibodies, as well as chimeric antigen receptors (CAR). This is at least because of these antibodies' enhanced therapeutic index and their small sizes.

Accordingly, in one embodiment, provided is a bispecific antibody that includes an anti-4-1BB nanobody of the present disclosure, or an antigen-binding fragment thereof, and a second antibody or antigen-binding fragment having binding specificity to a target antigen that is not 4-1BB. In some embodiment, a third or fourth specificity is further included.

The target antigen that is not 4-1BB, in some embodiments, is a tumor antigen. An abundance of tumor antigens are known in the art and new tumor antigens can be readily identified by screening. Non-limiting examples of tumor antigens include ABL, ALK, B4GALNT1, BAFF, BCL2, BRAF, BTK, CD19, CD20, CD30, CD38, CD52, CD73, Claudin 18.2, CTLA-4, EGFR, FOLR1, FLT3, HDAC, HER2, IDH2, IL-1β, IL-6, IL-6R, JAK1/2, JAK3, KIT, LAG-3, MEK, Nectin 4, ROR1, mTOR, PARP, PD-1, PDGFR, PDGFRα, PD-L1, PI3Kδ, PIGF, PTCH, RAF, RANKL, Smoothened, VEGF, VEGFR, and VEGFR2. Other examples are Her2, EpCAM, CD33, CD47, CD133, CEA, gpA33, Mucins, TAG-72, CIX, PSMA, GD2, GD3, GM2, Integrin, αVβ3, α5β1, ERBB2, ERBB3, MET, IGF1R, EPHA3, TRAILR1, TRAILR2, RANKL, FAP and Tenascin.

Also provided, are chimeric antigen receptor (CAR) that includes a nanobody of the present disclosure. In the CAR, the nanobody can serve as the antigen recognition domain. In addition, in some embodiments, the CAR also includes an extracellular hinge region, a transmembrane domain, and an intracellular T-cell signaling domain.

The hinge, also called a spacer, is a small structural domain that sits between the antigen recognition region and the cell's outer membrane. A suitable hinge enhances the flexibility of the scFv receptor head, reducing the spatial constraints between the CAR and its target antigen. Example hinge sequences are based on membrane-proximal regions from immune molecules such as IgG, CD8, and CD28.

The transmembrane domain is a structural component, consisting of a hydrophobic alpha helix that spans the cell membrane. It anchors the CAR to the plasma membrane, bridging the extracellular hinge and antigen recognition domains with the intracellular signaling region. Typically, the transmembrane domain from a membrane-proximal component of the endodomain can be used, such as the CD28 transmembrane domain.

The intracellular T-cell signaling domain lies in the receptor's endodomain, inside the cell. After an antigen is bound to the external antigen recognition domain, CAR receptors cluster together and transmit an activation signal. Then the internal cytoplasmic end of the receptor perpetuates signaling inside the T cell. To mimic this process, CD3-zeta's cytoplasmic domain is commonly used as the main CAR endodomain component.

T cells also require co-stimulatory molecules in addition to CD3 signaling in order to persist after activation. In some embodiments, the endodomains of CAR receptor also includes one or more chimeric domains from co-stimulatory proteins, such as CD28, CD27, CD134 (OX40), and CD137 (4-1BB).

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Cancer Treatment

As described herein, the antibodies, bispecific antibodies, polypeptides, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

In some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express a tumor antigen.

Cellular therapies, such as chimeric antigen receptor (CAR) T-cell or NK cell therapies, are also provided in the present disclosure. A suitable cell can be used, that is put in contact with an antibody or CAR of the present disclosure (or alternatively engineered to express an antibody or CAR of the present disclosure). Upon such contact or engineering, the cell can then be introduced to a cancer patient in need of a treatment. The cancer patient may have a cancer of any of the types as disclosed herein. The cell (e.g., T cell or NK cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Diagnostic Methods

Over-expression of 4-1BB is observed in certain tumor samples, and patients having 4-1BB-over-expressing cells are likely responsive to treatments with the anti-4-1BB antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a 4-1BB protein potentially present in the sample. Methods such as ELISA can be used, taking advantage of the anti-4-1BB antibody, to detect the presence of the 4-1BB protein in the sample.

Presence of the 4-1BB protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

EXAMPLES

Example 1: Generation of Nanobodies Against Human 4-1BB

This example describes the generations of nanobodies against the human 4-1BB protein.

Llamas were immunized with recombinant ECD of human 4-1BB fused to a human immunoglobulin Fc domain. Llamas whose sera contained sufficient titers of anti-4-1BB antibody were selected for generation of phage libraries. Briefly, lymphocytes were isolated from peripheral blood collected from immunized llamas. The lymphocyte RNA was extracted and cDNA encoding VHH domains was amplified by PCR and used for the construction of M13 phage-display-based nanobody libraries. Several rounds of panning were applied to screen the phage libraries expressing anti-4-1BB nanobodies.

All the positive clones were screened through ELISA and FACS assays prior to sequencing. Based on the sequence diversity, 16 unique clones were selected, the sequences of which are shown in Table. 1. The anti-4-1BB nanobodies fused with human IgG1 Fc fragment with N297A mutation at the C-terminus were characterized for their specificity and activity through a series of functional assays including binding, ligand competition and 4-1BB signal activation which resulted in the identification of lead nanobodies for further humanization.

TABLE 1

Sequences of the selected 16 unique clones.

| Antibody | Sequence | SEQ ID NO: |
|---|---|---|
| VV02-1LP-317 | EVDLVESGGGLVQPGGSLRLSCAASGFTFSRSAMSWARQAPGKGFEWVSG IYSGGSTYYVDSVEGRFTISRDNAKNTVYLQMNSLKPEDTAVYYCATWGS QQIGVWHEDDYWGQGTQVTVSS | 1 |
| VV02-1LP-263 | EVQLVESGGGLVQPGGSLRLSCAASGFTFSSSAMSWARQTPGKGFEWVSG IYSDGSTYYTDSVKDRFTISRDNAKNTVYLQMNSLKPEDTAVYYCATWGT LRFGVWAEYDHWGQGTQVTVSS | 2 |
| VV02-1LP-355 | QVQLVESGGGLVQPGGSLRLSCAASGFTFSSSAMSWARQAPGKDFEWVSY IYSDGNTYYADSVKGRFTISRDNAKNTVYLQMNSLKPEDTAVYYCATWHT LRVGVWDEYDYWGQGTQVTVSS | 3 |
| VV02-3LP-66 | QLQLVESGGGLVQPGGSLRLSCAASGFTFSSSAMSWARQAPGKEFEWVSY IYSDGNTYYTDSVKGRFTVSRDNAKNTVYLQMNSLKPEDTAVYYCATWNS LQVGVWDEYDYWGQGTQVTVSS | 4 |
| VV02-1LP-265 | EVQLVESGGGLVQPGGSLRLSCAASGFTFSSSAMSWARQVPGKGFEWVAY IYSDGSTYYADSVKGRFTISRDNAKDTVYLHMNSLKFEDMAVYYCATWRS QQVGRWDEYDHWGQGTQVTVSS | 5 |
| VV02-2LP-13 | AVQLVESGGGLVQPGGSLRLSCAASGFTFSSYAMSWARQVPGKGFEWVAY IYSDGSTYYADSVKGRFTISRDNAKDTVYLHMNSLKFEDMAVYYCATWRS QQVGRWDEYDHWGQGTQVTVSS | 6 |
| VV02-3LP-142 | AVQLVESGGGLVQRGGSLKLSCVGSGFDFSDHAMSWARQVPGKGFEWVAY IYSDGSTYYADSVKGRFTISRDNAKDTVYLHMNSLKFEDMAVYYCATWRS QQVGRWDEYDHWGQGTQVTVSS | 7 |
| VV02-3LP-83 | EVDLVESGGGLVQPGGSLRLSCAASGFTFRSYAMSWARQVPGKGFEWVAY IYSDGSTYYADSVKGRFTISRDNAKDTVYLHMNSLKFEDMAVYYCATWRS QQVGRWDEYDHWGQGTQVTVSS | 8 |
| VV02-1LP-417 | QLQLVESGGGLVQPGGSLRLSCAASGFALDYSAIGWFRQAPGKEREGVLC ISSSGDVTIYADSVKGRFTISRDNAKNTVYLQMNSLKPEDTAVYYCVAPR ICSTYSSDDYWGQGTQVTVSS | 9 |
| VV02-1LP-422 | QLQLVESGGGLVQPGGSLRLSCAASGFTLADYAIGWFRQAPGKEREGVLC ISSSGDVTIYADSVKGRFTISRDNAKNTVYLQMNSLKPEDTAVYYCVAPR ICSTYSSDDYWGQGTQVTVSS | 10 |
| VV02-1LP-238 | QVQLVESGGGLVQAGGALRLSCAASGFTLDYSAIGWFRQAPGKEREGVLC ISSSGDVTIYADSVKGRFTISRDNAKNTVYLQMNSLKPEDTAVYYCVAPR ICSTYSSDDYWGQGTQVTVSS | 11 |
| VV02-1LP-288 | EVQVVESGGGLVQPGGSLRLSCAASGSSLDYSAIGWFRQAPGKEREGVLC ISSSGDVTIYADSVKGRFTISRDNAKNTVYLQMNSLKPEDTAVYYCVAPR ICSTYSSDDYWGQGTQVTVSS | 12 |
| VV02-1SP (1)-168 | QVQLVESGGGLVQPGGSLRLSCAASGFTFSSYAMSWARQAPGKDFEWVSY IYSDGNTYYADSVKGRFTISRDNAKNTVYLQMNSLKPEDTAVYYCATWHT LRVGVWDEYDYWGQGTQVTVSS | 13 |

TABLE 1-continued

Sequences of the selected 16 unique clones.

| Antibody | Sequence | SEQ ID NO: |
|---|---|---|
| VV02-1SP (1)-55 | EVQLVESGGGLVQPGGSLRLSCAASGFTFSSSAMSWARQVPGKGFEWVAYIYSDGSTYYADSVKGRFTISRDNAKDTVYLHMNSLKFEDMAVYYCATWRSQQVGRWDEYDYWGQGIQVTVSS | 14 |
| VV02-1SP (1)-73 | EVDLVESGGGLVQPGGSLRLSCAVSGFTFSNSAMSWARQAPGKEFEWVSSIYSDGKTYYVDSVKGRFTISRDNAKNTVYLQMSSLKPEDTAVYYCATWKTLRVGVWDESDYWGQGTQVTVSS | 15 |
| VV02-1SP (1)-358 | EVQLVESGGGLVQPGGSLMISCAASGFTFSSSAMSWARQVPGKGFEWVAYIYSDGSTYYADSVKGRFTISRDNAKDTVYLHMNSLKFEDMAVYYCATWRSQQVGRWDKYDYWGQGTQVTVSS | 16 |

Their CDR sequences are summarized in Table 1A below.

TABLE 1A

Sequences of the selected 16 unique clones.

| Antibody | CDR1 | SEQ ID NO: | CDR2 | SEQ ID NO: | CDR3 | SEQ ID NO: |
|---|---|---|---|---|---|---|
| VV02-1LP-317 | RSAMS | 17 | GIYSGGSTYYVDSVEG | 24 | WGSQQIGVWHEDDY | 31 |
| VV02-1LP-263 | SSAMS | 18 | GIYSDGSTYYTDSVKD | 25 | WGTLRFGVWAEYDH | 32 |
| VV02-1LP-355 | SSAMS | 18 | YIYSDGNTYYADSVKG | 26 | WHTLRVGVWDEYDY | 33 |
| VV02-3LP-66 | SSAMS | 18 | YIYSDGNTYYTDSVKG | 27 | WNSLQVGVWDEYDY | 34 |
| VV02-1LP-265 | SSAMS | 18 | YIYSDGSTYYADSVKG | 28 | WRSQQVGRWDEYDH | 35 |
| VV02-2LP-13 | SYAMS | 19 | YIYSDGSTYYADSVKG | 28 | WRSQQVGRWDEYDH | 35 |
| VV02-3LP-142 | DHAMS | 20 | YIYSDGSTYYADSVKG | 28 | WRSQQVGRWDEYDH | 35 |
| VV02-3LP-83 | SYAMS | 19 | YIYSDGSTYYADSVKG | 28 | WRSQQVGRWDEYDH | 35 |
| VV02-1LP-417 | YSAIG | 21 | CISSSGDVTIYADSVKG | 29 | PRICSTYSSDDY | 36 |
| VV02-1LP-422 | DYAIG | 22 | CISSSGDVTIYADSVKG | 29 | PRICSTYSSDDY | 36 |
| VV02-1LP-238 | YSAIG | 21 | CISSSGDVTIYADSVKG | 29 | PRICSTYSSDDY | 36 |
| VV02-1LP-288 | YSAIG | 21 | CISSSGDVTIYADSVKG | 29 | PRICSTYSSDDY | 36 |
| VV02-1SP (1)-168 | SYAMS | 19 | YIYSDGNTYYADSVKG | 26 | WHTLRVGVWDEYDY | 33 |
| VV02-1SP (1)-55 | SSAMS | 18 | YIYSDGSTYYADSVKG | 28 | WRSQQVGRWDEYDY | 37 |
| VV02-1SP (1)-73 | NSAMS | 23 | SIYSDGKTYYVDSVKG | 30 | WKTLRVGVWDESDY | 38 |
| VV02-1SP (1)-358 | SSAMS | 18 | YIYSDGSTYYADSVKG | 28 | WRSQQVGRWDKYDY | 39 |

Antibodies VV02-1LP-417, VV02-1LP-422, VV02-1LP-238, and VV02-1LP-288 appear to share very similar CDRs, while the remaining ones also have homologous CDRs.

Example 2. Soluble 4-1BB Binding Properties of Anti-4-1BB Nanobodies

This example tested the binding properties of the resulting anti-4-1BB nanobodies to human and cynomolgus 4-1BB proteins by ELISA assay.

Figure 1B:
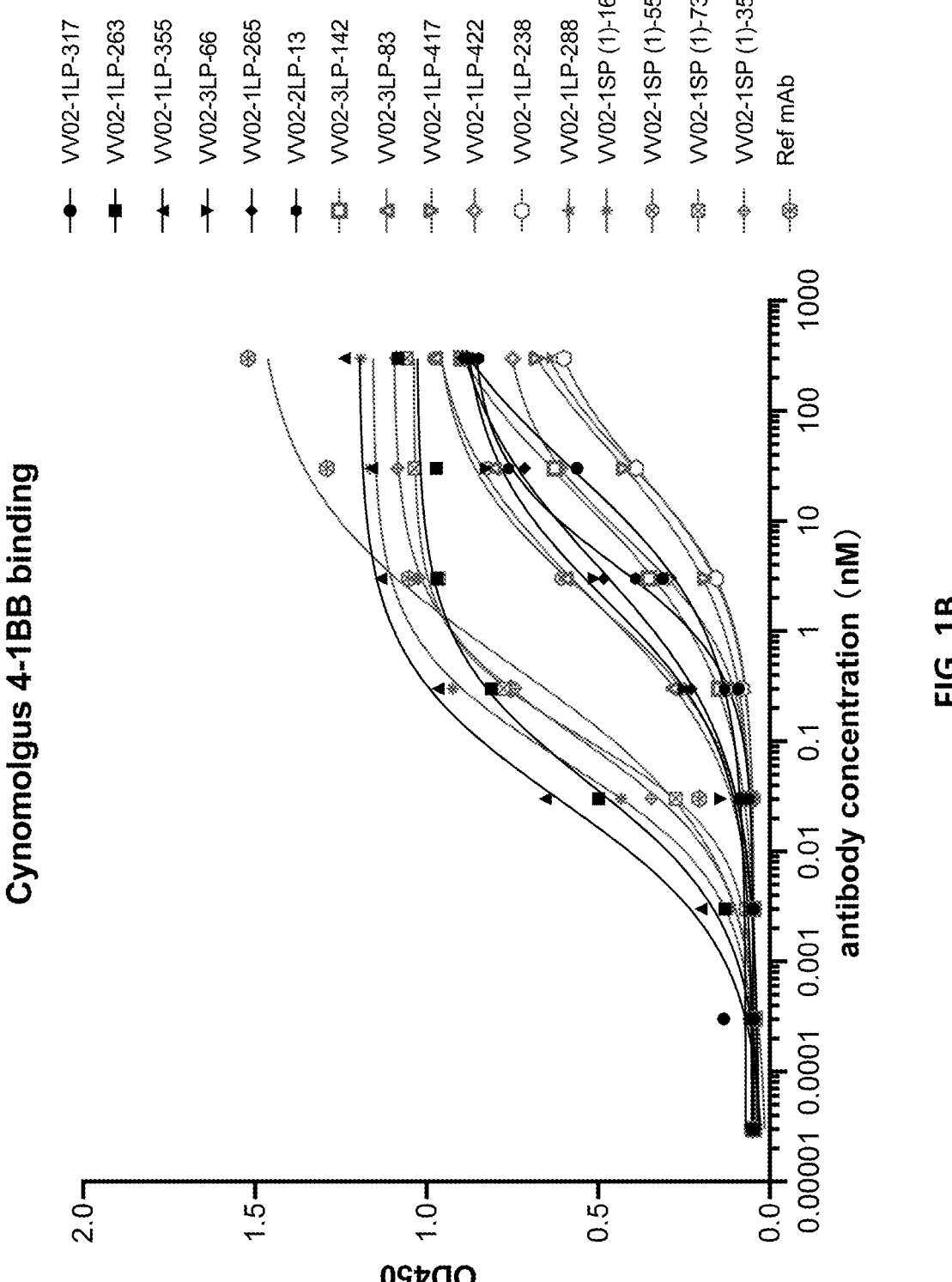

His-tagged 4-1BB was coated at 2 μg/ml overnight and then blocked by 2% BSA in PBS. Serially diluted anti-4-1BB nanobodies were incubated with the coated antigen for 1 at room temperature with a reference antibody "Ref mAb". The resulting plates were washed with PBS/T and incubated with goat anti-human IgG-HRP for 1 h at room temperature. The plates were developed with TMB substrate and analyzed by spectrophotometer at OD 450 nm. The results of the ELISA assays are showed in FIG. 1 and Table. 2, which shows $EC_{50}$ of binding to human and cynomolgus 4-1BB protein.

TABLE 2

Binding $EC_{50}$ (nM) on human and Cyno 4-1BB protein.

| Antibody | hu4-1BB $EC_{50}$(nM) | Cyno 4-1BB $EC_{50}$ (nM) |
|---|---|---|
| VV02-1LP-317 | >30 | 29.32 |
| VV02-1LP-263 | >30 | 0.04 |
| VV02-1LP-355 | 23.97 | 0.03 |
| VV02-3LP-66 | >30 | 1.95 |
| VV02-1LP-265 | >30 | 3.86 |
| VV02-2LP-13 | >30 | 4.19 |
| VV02-3LP-142 | >30 | 18.24 |
| VV02-3LP-83 | >30 | 2.03 |
| VV02-1LP-417 | 11.11 | >30 |
| VV02-1LP-422 | 0.37 | 6.94 |
| VV02-1LP-238 | 9.12 | 26.46 |
| VV02-1LP-288 | >30 | >30 |
| VV02-1SP (1)-168 | >30 | 0.06 |
| VV02-1SP (1)-55 | >30 | 1.87 |
| VV02-1SP (1)-73 | >30 | 0.11 |
| VV02-1SP (1)-358 | >30 | 0.11 |
| Ref mAb | 18.77 | 0.51 |

Example 3. Blocking 4-1BB/4-1BB Ligand Interaction by Anti-41BB Nanobodies

In this example, the anti-41BB nanobodies were examined for their ability to block the binding of 4-1BB to its ligand.

Figure 2:
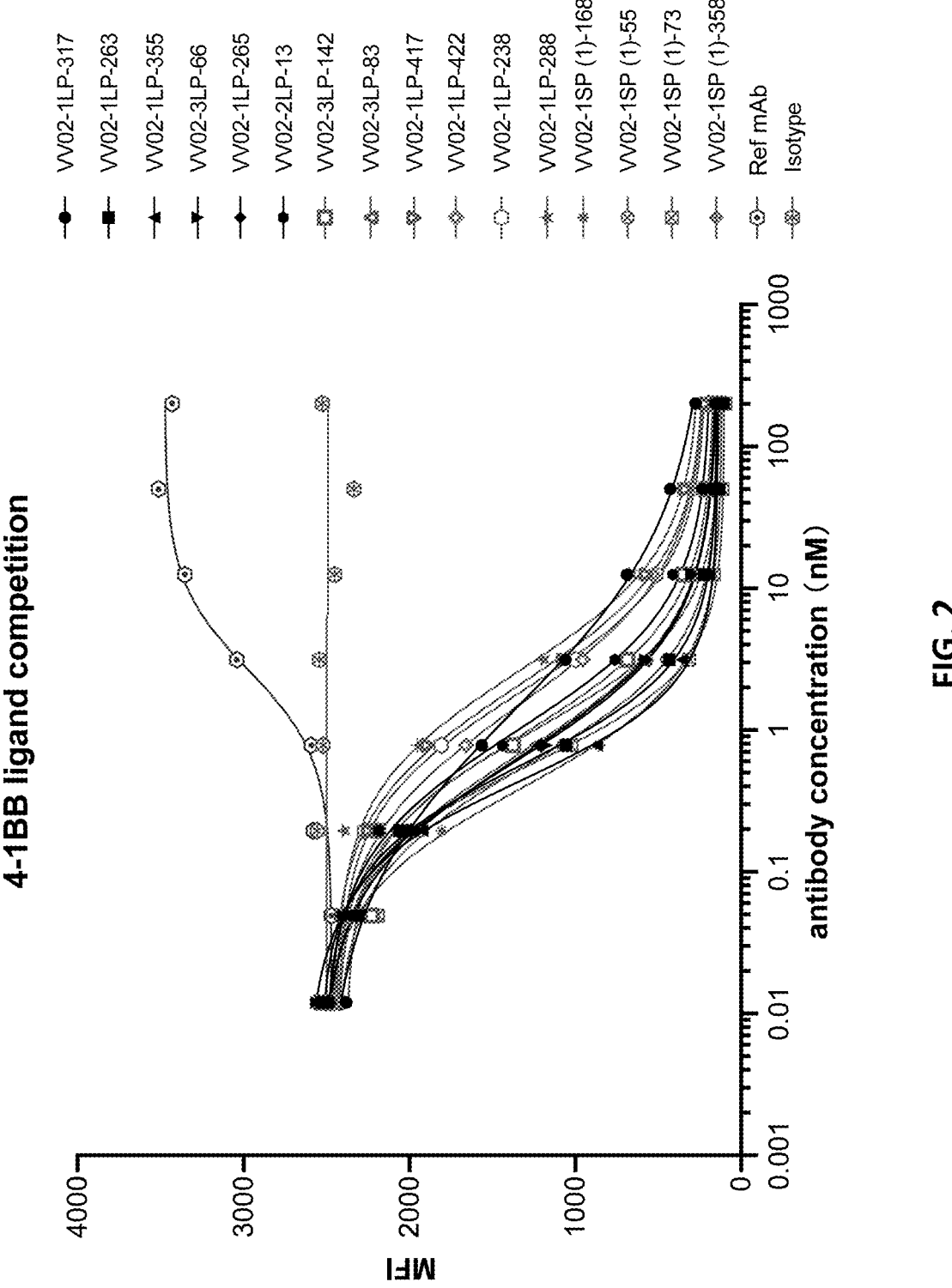
FIG. 2 shows that the anti-41BB nanobodies could block 4-1BB ligand binding to 4-1BB in a concentration-dependent manner.

CHO-K1 cells overexpressing human 4-1BB were incubated with biotinylated human 4-1BB ligand (0.3 μg/ml) in the presence of serial diluted anti-41BB nanobodies for 1 h at 4° C. with Ref mAb as the reference antibody. Then, cells were incubated with Alexa Fluor 633-conjugated streptavidin. Binding was measured with an Agilent flow cytometer. As shown in FIG. 2 and Table 3, all of the tested nanobodies could block 4-1BB ligand binding to 4-1BB in a concentration-dependent manner while Ref mAb had no such effect.

TABLE 3

Competition $IC_{50}$ (nM) on 4-1BB/4-1BB ligand interaction

| Antibody | $IC_{50}$ (nM) |
|---|---|
| VV02-1LP-317 | 1.416 |
| VV02-1LP-263 | 0.566 |
| VV02-1LP-355 | 0.4346 |
| VV02-3LP-66 | 0.5733 |
| VV02-1LP-265 | 0.6417 |
| VV02-2LP-13 | 0.9945 |
| VV02-3LP-142 | 0.9233 |
| VV02-3LP-83 | 0.6824 |
| VV02-1LP-417 | 2.053 |
| VV02-1LP-422 | 1.484 |
| VV02-1LP-238 | 1.876 |
| VV02-1LP-288 | 2.573 |
| VV02-1SP (1)-168 | 0.3873 |
| VV02-1SP (1)-55 | 0.5729 |
| VV02-1SP (1)-73 | 0.5725 |
| VV02-1SP (1)-358 | 0.9879 |
| Ref mAb | 2.657 |

Example 4. Functional Property of Anti-41BB Nanobodies in a Jurkat-41BB NFκB Reporter Assay This example evaluated the functional property of the anti-41BB nanobodies in a 4-1BB reporter assay.

In this assay, the effector cells were 4-1BB NFκB-reporter Jurkat cell line which stably expresses human 4-1BB and has an NFκB luciferase reporter construct integrated into the genome. Following 4-1BB activation, endogenous NFκB transcription factors bind to the DNA response elements to induce transcription of the luciferase gene, whose protein product is then quantified by measuring the luminescence signal. 4-1BB NFκB-reporter Jurkat cell line was cocultured with target cell line CHO-K1 or FcγRIIB-CHO-K1 cell line which overexpressed human Fcγ receptor II B. Antibodies were serially diluted and added to a white 96-well assay plate. After 16 hours of incubation at 37° C., luminescence was obtained by adding the substrate of luciferase and measured by a microplate reader.

Figure 3A:
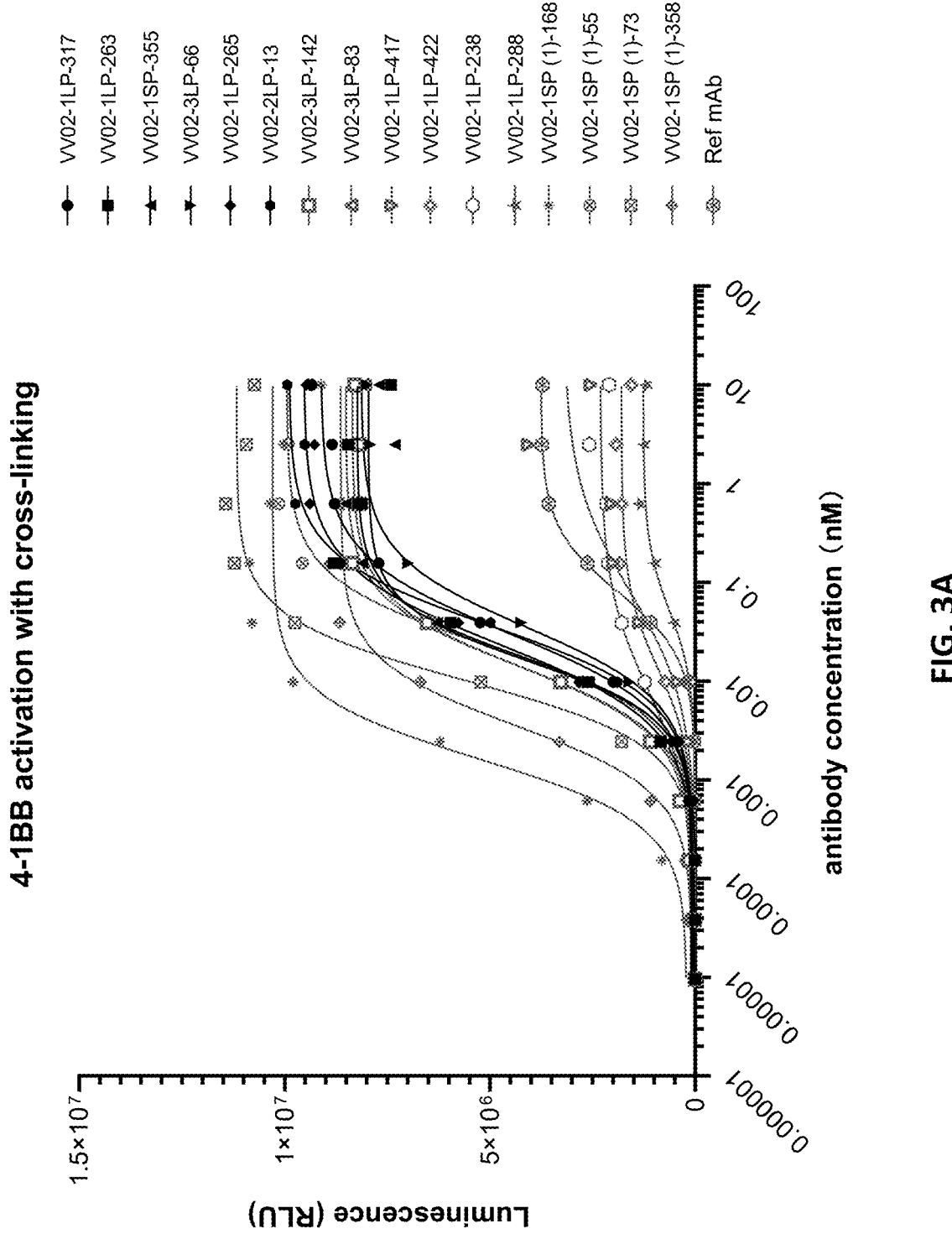
FIG. 3A-B show that the anti-41BB nanobodies efficiently induced 4-1BB-mediated NFκB activity in the presence of Fc crosslinking.
Figure 3B:
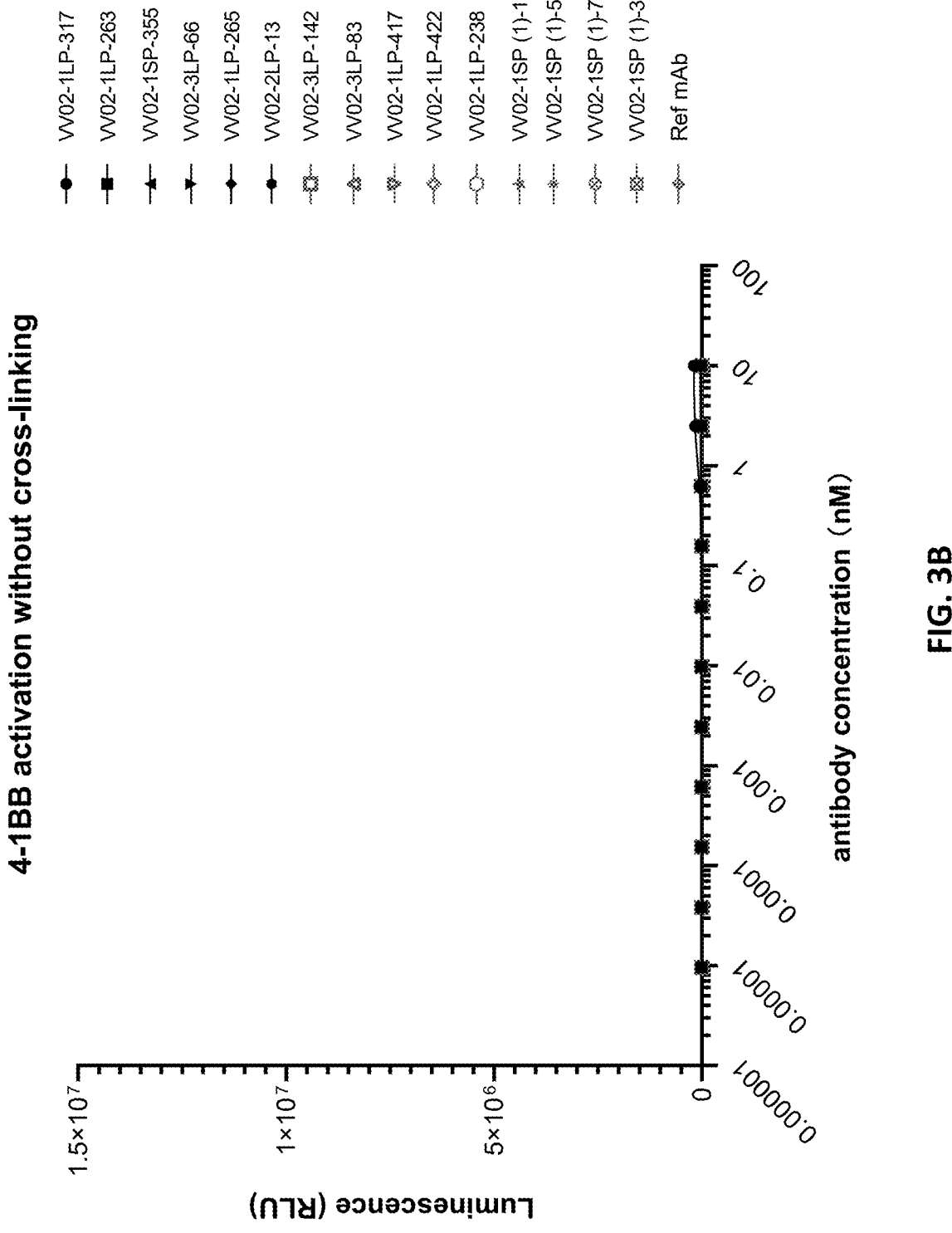

As shown in FIG. 3 and Table 4, the tested 4-1BB nanobodies induced 4-1BB-mediated NF-κB activity in the presence of Fc crosslinking with an $EC_{50}$ range from 0.002 nM to 0.081 nM. However, when Fc crosslinking was absent, the tested antibodies were not able to activate NF-κB signal.

TABLE 4

$EC_{50}$ (nM) in Jurkat-41BB NFκB reporter assay

| Antibody | $EC_{50}$(nM) |
|---|---|
| VV02-1LP-317 | 0.031 |
| VV02-1LP-263 | 0.017 |
| VV02-1LP-355 | 0.016 |
| VV02-3LP-66 | 0.035 |
| VV02-1LP-265 | 0.024 |

US 12,692,318 B2

19

TABLE 4-continued

| EC$_{50}$ (nM) in Jurkat-41BB NFκB reporter assay | |
|---|---|
| Antibody | EC$_{50}$(nM) |
| VV02-2LP-13 | 0.036 |
| VV02-3LP-142 | 0.014 |
| VV02-3LP-83 | 0.014 |
| VV02-1LP-417 | 0.081 |
| VV02-1LP-422 | 0.013 |
| VV02-1LP-238 | 0.008 |
| VV02-1LP-288 | 0.052 |
| VV02-1SP (1)-168 | 0.002 |
| VV02-1SP (1)-55 | 0.023 |
| VV02-1SP (1)-73 | 0.010 |

20

TABLE 4-continued

| EC$_{50}$ (nM) in Jurkat-41BB NFκB reporter assay | |
|---|---|
| Antibody | EC$_{50}$(nM) |
| VV02-1SP (1)-358 | 0.004 |
| Ref mAb | 0.080 |

Example 5. Anti-41BB Nanobody Humanization

Humanization of lead nanobodies (VV02-1LP-263 and VV02-1SP (1)-73) was conducted by CDR grafting and back-mutation strategy. The humanized sequences of which are shown in Table. 5.

TABLE 5

Sequences of humanized lead nanobodies.

| Antibody | Sequence | SEQ ID NO: |
|---|---|---|
| VV02-1LP-263 huNb_1_1 | EVQLLESGGGLVQPGGSLRLSCAASGFTFSSSAMSWARQAPGKGLEWVSG IYSGGSTYYTESVKDRFTISRDNSKNTLYLQMNSLRAEDTAVYYCAKWGT LRFGVWAEYDHWGQGTLVTVSS | 40 |
| VV02-1LP-263 huNb_1_2 | EVQLLESGGGLVQPGGSLRLSCAASGFTFSSSAMSWARQAPGKGLEWVSG IYSGGSTYYTESVKDRFTISRDNSKNTVYLQMNSLKPEDTAVYYCATWGT LRFGVWAEYDHWGQGTLVTVSS | 41 |
| VV02-1LP-263 huNb_1_3 | EVQLLESGGGLVQPGGSLRLSCAASGFTFSSSAMSWARQTPGKGFEWVSG IYSGGSTYYTESVKDRFTISRDNSKNTVYLQMNSLKPEDTAVYYCATWGT LRFGVWAEYDHWGQGTQVTVSS | 42 |
| VV02-1LP-263 huNb_2_1 | EVQLLESGGGLVQPGGSLRLSCAASGFTFSSSAMSWARQAPGKGFEWVSG IYSGGSTYYTESVKDRFTISRDNSKNTLYLQMNSLRAEDTAVYYCAKWGT LRFGVWAEYDHWGQGTLVTVSS | 43 |
| VV02-1LP-263 huNb_2_2 | EVQLVESGGGLVQPGGSLRLSCAASGFTFSSSAMSWARQAPGKGLEWVSG IYSGGSTYYTESVKDRFTISRDNAKNTLYLQMNSLRPEDTAVYYCATWGT LRFGVWAEYDHWGQGTLVTVSS | 44 |
| VV02-1LP-263 huNb_2_3 | EVQLVESGGGLVQPGGSLRLSCAASGFTFSSSAMSWARQAPGKGFEWVSG IYSGGSTYYTESVKDRFTISRDNAKNTVYLQMNSLKPEDTAVYYCATWGT LRFGVWAEYDHWGQGTLVTVSS | 45 |
| VV02-1LP-263 huNb_3_1 | QVQLVESGGGLVKPGGSLRLSCAASGFTFSSSAMSWARQAPGKGLEWVSG IYSGGSTYYTESVKDRFTISRDNAKNSLYLQMNSLRAEDTAVYYCARWGT LRFGVWAEYDHWGQGTLVTVSS | 46 |
| VV02-1LP-263 huNb_3_2 | QVQLVESGGGLVKPGGSLRLSCAASGFTFSSSAMSWARQAPGKGFEWVSG IYSGGSTYYTESVKDRFTISRDNAKNSLYLQMNSLRPEDTAVYYCATWGT LRFGVWAEYDHWGQGTQVTVSS | 47 |
| VV02-1LP-263 huNb_3_3 | QVQLVESGGGLVQPGGSLRLSCAASGFTFSSSAMSWARQAPGKGFEWVSG IYSGGSTYYTESVKDRFTISRDNAKNSVYLQMNSLKPEDTAVYYCATWGT LRFGVWAEYDHWGQGTQVTVSS | 48 |
| VV02-1SP (1)- 73 huNb_1_1 | EVQLLESGGGLVQPGGSLRLSCAASGFTFSSSAMSWARQAPGKGLEWVSS IYSSGKTYYVESVKGRFTISRDNSKNTLYLQMNSLRAEDTAVYYCAKWKT LRVGVWDESDYWGQGTLVTVSS | 49 |
| VV02-1SP (1)- 73 huNb_1_2 | EVQLLESGGGLVQPGGSLRLSCAASGFTFSSSAMSWARQAPGKELEWVSS IYSSGKTYYVESVKGRFTISRDNAKNTLYLQMSSLRAEDTAVYYCATWKT LRVGVWDESDYWGQGTLVTVSS | 50 |
| VV02-1SP (1)- 73 huNb_1_3 | EVDLVESGGGLVQPGGSLRLSCAVSGFTFSSSAMSWARQAPGKEFEWVSS IYSSGKTYYVESVKGRFTISRDNAKNTVYLQMSSLRPEDTAVYYCATWKT LRVGVWDESDYWGQGTLVTVSS | 51 |
| VV02-1SP (1)- 73 huNb_2_1 | EVQLVESGGGLIQPGGSLRLSCAASGFTFSSSAMSWARQAPGKGFEWVSS IYSSGKTYYVESVKGRFTISRDNSKNTLYLQMNSLRAEDTAVYYCARWKT LRVGVWDESDYWGQGTLVTVSS | 52 |
| VV02-1SP (1)- 73 huNb_2_2 | EVQLVESGGGLIQPGGSLRLSCAASGFTFSSSAMSWARQAPGKEFEWVSS IYSSGKTYYVESVKGRFTISRDNAKNTLYLQMSSLRAEDTAVYYCATWKT LRVGVWDESDYWGQGTQVTVSS | 53 |

TABLE 5-continued

| | | SEQ ID NO: |
|---|---|---|
| Antibody | Sequence | |
| VV02-1SP (1)-73 huNb_2_3 | EVQLVESGGGLVQPGGSLRLSCAVSGFTFSSSAMSWARQAPGKEFEWVSS IYSSGKTYYVESVKGRFTISRDNAKNTVYLQMSSLRPEDTAVYYCATWKT LRVGVWDESDYWGQGTQVTVSS | 54 |
| VV02-1SP (1)-73 huNb_3_1 | EVQLVESGGGLVQPGGSLRLSCAASGFTFSSSAMSWARQAPGKGFEWVAS IYSSGKTYYVESVKGRFTISRDNAKNSLYLQMNSLRAEDTAVYYCARWKT LRVGVWDESDYWGQGTLVTVSS | 55 |
| VV02-1SP (1)-73 huNb_3_2 | EVQLVESGGGLVQPGGSLRLSCAASGFTFSSSAMSWARQAPGKGFEWVSS IYSSGKTYYVESVKGRFTISRDNAKNSLYLQMSSLRAEDTAVYYCATWKT LRVGVWDESDYWGQGTLVTVSS | 56 |
| VV02-1SP (1)-73 huNb_3_3 | EVQLVESGGGLVQPGGSLRLSCAVSGFTFSSSAMSWARQAPGKEFEWVSS IYSSGKTYYVESVKGRFTISRDNAKNSVYLQMSSLRPEDTAVYYCATWKT LRVGVWDESDYWGQGTLVTVSS | 57 |

For VV02-1LP-263, two mutations (D54G and D61E, Kabat numbering) were introduced to CDR2 to improve developability. For VV02-1SP (1)-73, a mutation (N31S, Kabat numbering) and two mutations (D54S and D61E, Kabat numbering) were introduced to the CDR1 and CDR2, respectively, to improve developability. The sequence comparisons are shown in Table 5A below.

TABLE 5A

| | | | | | | |
|---|---|---|---|---|---|---|
| | | | Updated CDRs | | | |
| Antibody | CDR1 | SEQ ID NO: | CDR2 | SEQ ID NO: | CDR3 | SEQ ID NO: |
| VV02-1LP-263 | SSAMS | 18 | GIYSDGSTYYTDSVKD | 25 | WGTLRFGVWAEYDH | 32 |
| VV02-1LP-263 Humanized | SSAMS | 18 | GIYSGGSTYYTESVKD | 58 | WGTLRFGVWAEYDH | 32 |
| VV02-1SP (1)-73 | NSAMS | 23 | SIYSDGKTYYVDSVKG | 30 | WKTLRVGVWDESDY | 38 |
| VV02-1SP (1)-73 Humanized | SSAMS | 18 | SIYSSGKTYYVESVKG | 59 | WKTLRVGVWDESDY | 38 |

Example 6. Cell Surface 4-1BB Binding Properties of Anti-4-1BB Humanized Nanobodies To evaluate the antigen binding property in a cell-based setting, the 4-1BB humanized nanobodies were analyzed for their binding to 4-1BB overexpressed on CHO-K1 cells by FACS.

Figure 4A:
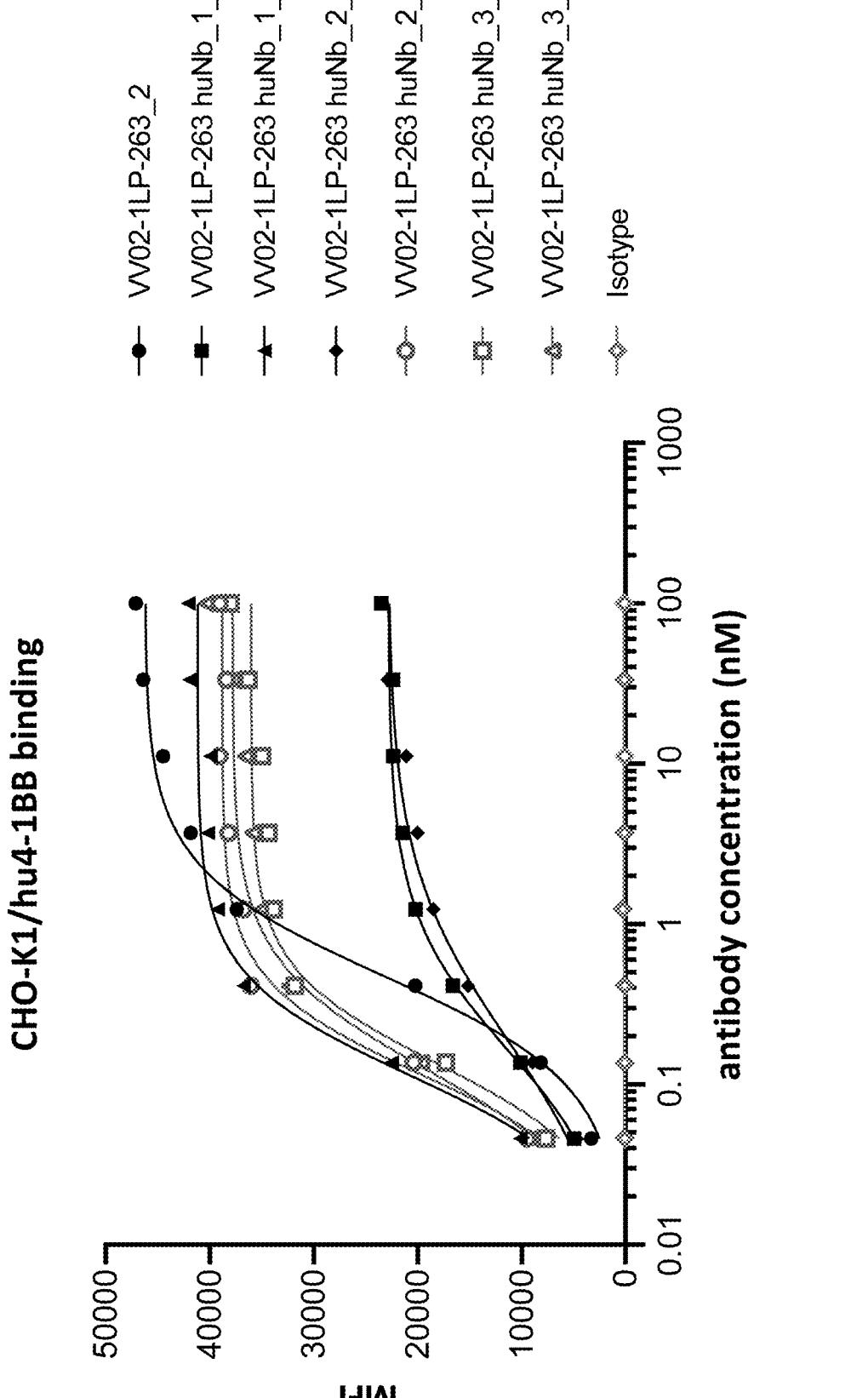
FIG. 4A-B show that the anti-41BB humanized nanobodies from parental clone VV02-1LP-263 bound to cell surface human or cynomolgus 4-1BB in a concentration-dependent manner.
Figure 4B:
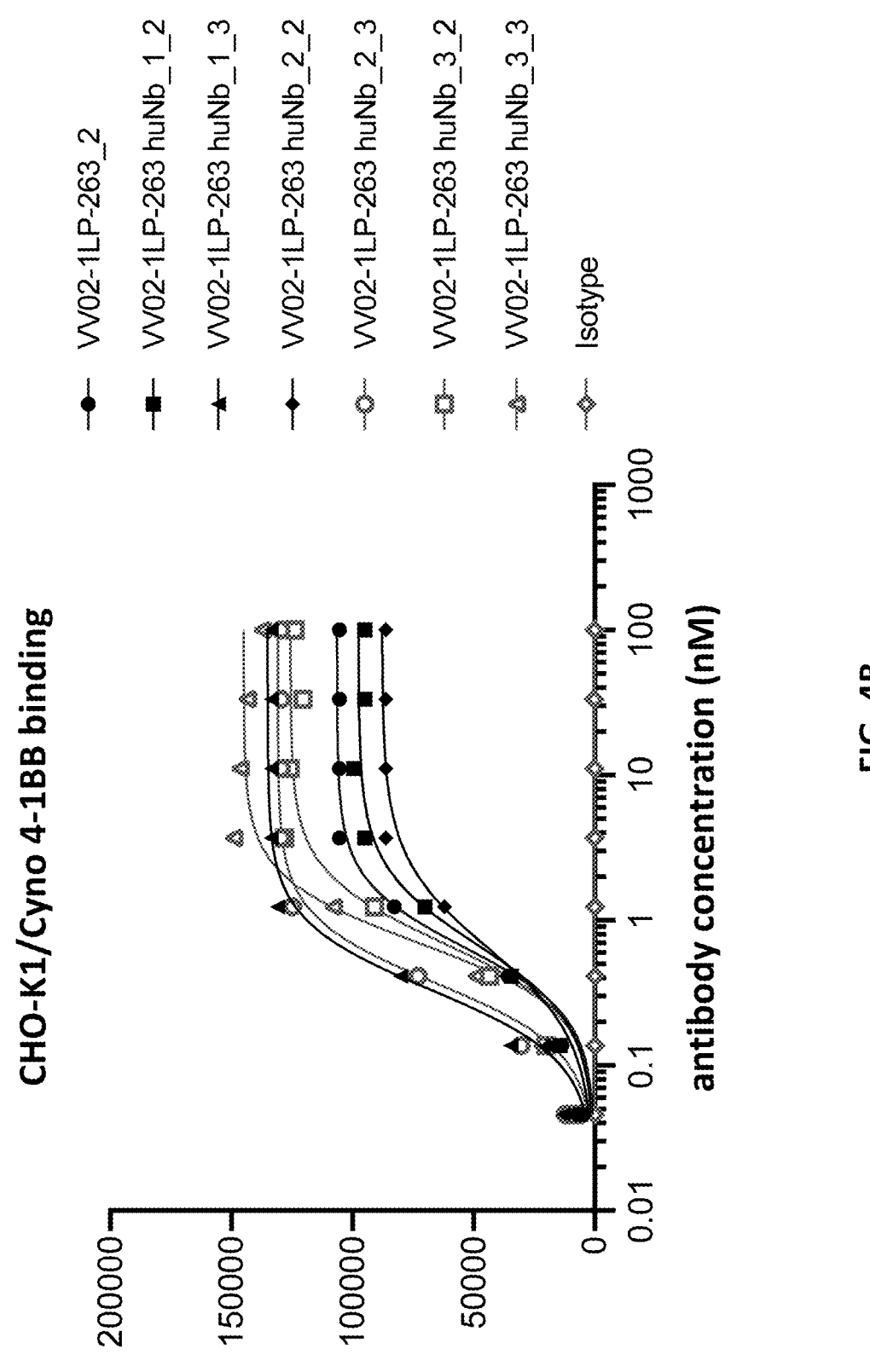
Figure 5:
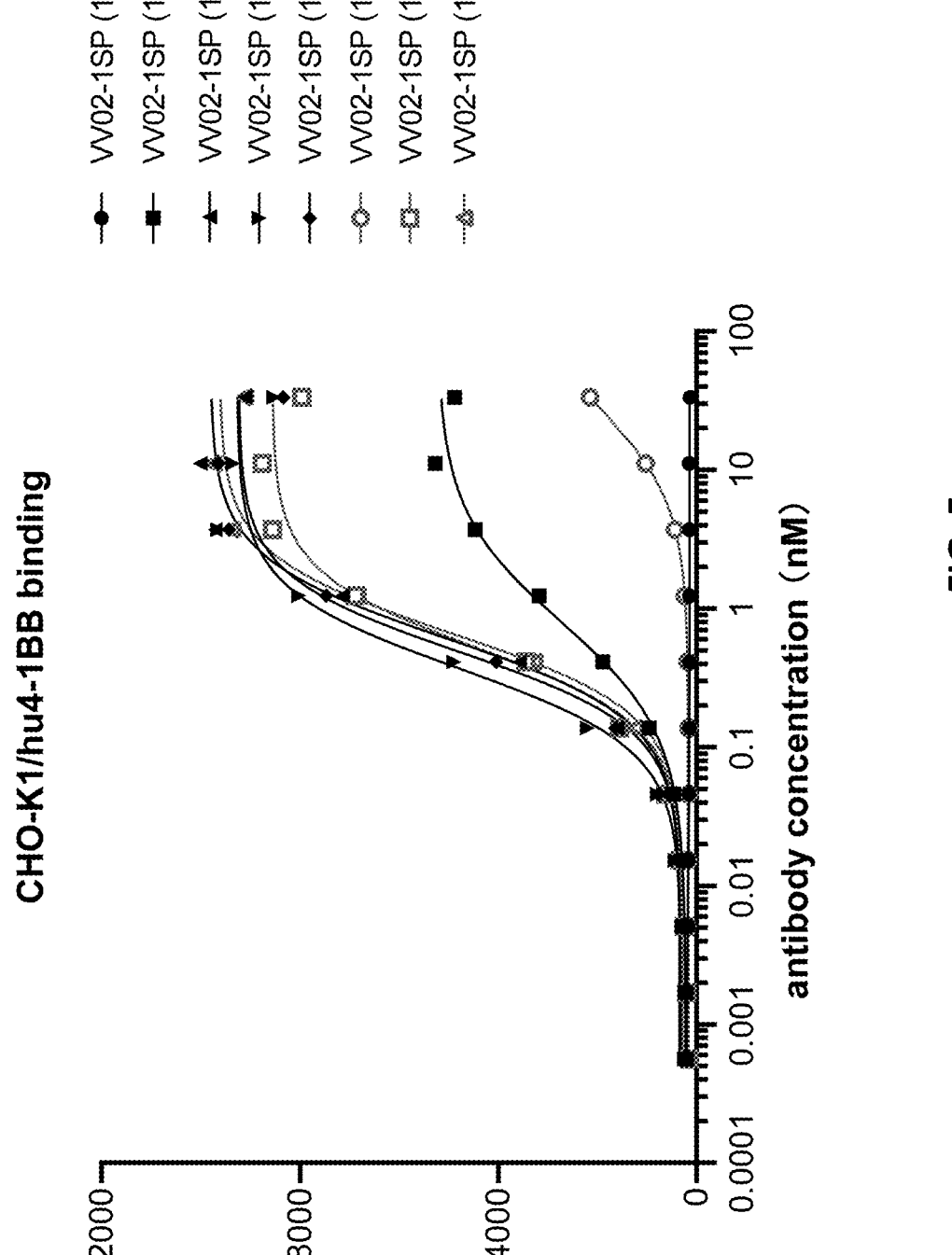
FIG. 5 shows that the anti-41BB humanized nanobodies from parental clone VV02-1SP (1)-73 bound to cell surface human 4-1BB in a concentration-dependent manner.

Briefly, CHO-K1 cells overexpressing human 4-1BB or cynomolgus 4-1BB were incubated with the serial diluted anti-4-1BB nanobodies for 30 min at 4° C. Then, the cells were incubated with Alexa Fluor 633-conjugated anti-human Fc secondary antibody. Binding was measured with an Agilent flow cytometer. The results showed that all the tested humanized nanobodies exhibited typical sigmoidal binding behavior against cell surface human 4-1BB and cyno 4-1BB (FIG. 4 & FIG. 5). The binding $EC_{50}$ are shown in Table 6 & Table 7 accordingly.

TABLE 6

Binding $EC_{50}$ (nM) on cell surface 4-1BB of humanized nanobodies from parental clone VV02-1LP-263.

| | CHO-K1/hu4-1BB | | CHO-K1/Cyno-41BB | |
|---|---|---|---|---|
| | $EC_{50}$ (nM) | Max (MFI) | $EC_{50}$ (nM) | Max (MFI) |
| VV02-1LP-263_2 | 0.47 | 47120 | 0.64 | 105589 |
| VV02-1LP-263 huNb_1_2 | 0.17 | 23533 | 0.69 | 99611 |
| VV02-1LP-263 huNb_1_3 | 0.11 | 42059 | 0.33 | 133804 |
| VV02-1LP-263 huNb_2_2 | 0.19 | 23409 | 0.64 | 86388 |
| VV02-1LP-263 huNb_2_3 | 0.11 | 39070 | 0.37 | 129678 |
| VV02-1LP-263 huNb_3_2 | 0.14 | 38041 | 0.70 | 128178 |
| VV02-1LP-263 huNb_3_3 | 0.12 | 40328 | 0.70 | 149247 |

TABLE 7

Binding $EC_{50}$ (nM) on cell surface 4-1BB of humanized nanobodies from parental clone VV02-1SP (1)-73.

| | CHO-K1/hu4-1BB | |
|---|---|---|
| | EC50 (nM) | Max (MFI) |
| VV02-1SP (1)-73 huNb_1_1 | — | 233.1 |
| VV02-1SP (1)-73 huNb_1_2 | 0.80 | 5243 |
| VV02-1SP (1)-73 huNb_1_3 | 0.61 | 9809 |
| VV02-1SP (1)-73 huNb_2_2 | 0.37 | 9270 |
| VV02-1SP (1)-73 huNb_2_3 | 0.49 | 9238 |
| VV02-1SP (1)-73 huNb_3_1 | 27.39 | 3700 |
| VV02-1SP (1)-73 huNb_3_2 | 0.52 | 8562 |
| VV02-1SP (1)-73 huNb_3_3 | 0.66 | 9627 |

Example 7. Sequence Optimization of Anti-4-1BB Nanobodies by Site-Mutation

To further increase developability of the candidates, anti-4-1BB nanobody VV02-1LP-263 huNb_1_3 was selected to be optimized by site-mutation. The optimized sequences are shown in Table 8.

TABLE 8

Optimized sequences of VV02-1LP-263 huNb_1_3

| Name | Sequence | SEQ ID NO: |
|---|---|---|
| 263 huNb-1-3_1 | EVQLVESGGGLVQPGGSLRLSCAASGFTF SSSAMSWARQAPGKGFEWVSGIYSGGSTY YTESVKDRFTISRDNSKNTVYLQMNSLKP EDTAVYYCATWGTLRFGVWAEYDHWGQGT QVTVSS | 60 |
| 263 huNb-1-3_2 | EVQLVESGGGLVQPGGSLRLSCAASGFTF SSSAMSWARQAPGKGFEWVSGIYSGGSTY YTESVKDRFTISRDNAKNTVYLQMNSLKP EDTAVYYCATWGTLRFGVWAEYDHWGQGT LVTVSS | 61 |
| 263 hnNb-1-3_3 | EVQLVESGGGLVQPGGSLRLSCAASGFTF SSSAMSWARQTPGKGFEWVSGIYSGGSTY YTESVKDRFTISRDNSKNTLYLQMNSLRP EDTAVYYCATWGTLRFGVWAEYDHWGQGT QVTVSS | 62 |

To evaluate the feasibility of optimized anti-4-1BB sequences to construct bi-specific antibody, the optimized anti-4-1BB was fused to the heavy chain C terminus of a IgG1 antibody targeting a tumor associated antigen (TAA) with N297A mutation in Fc fragment via G4S linker. Then, the light chain and heavy chain expression vectors were co-transfected into CHO-K1 cells. After transient transfection, the bispecific antibodies were purified from the medium by protein A affinity chromatography. The well qualified antibodies were applied to in vitro characterization including cell-based 4-1BB binding, 4-1BB activation and developability assessment.

Cell-Based 4-1BB Binding

Figure 6:
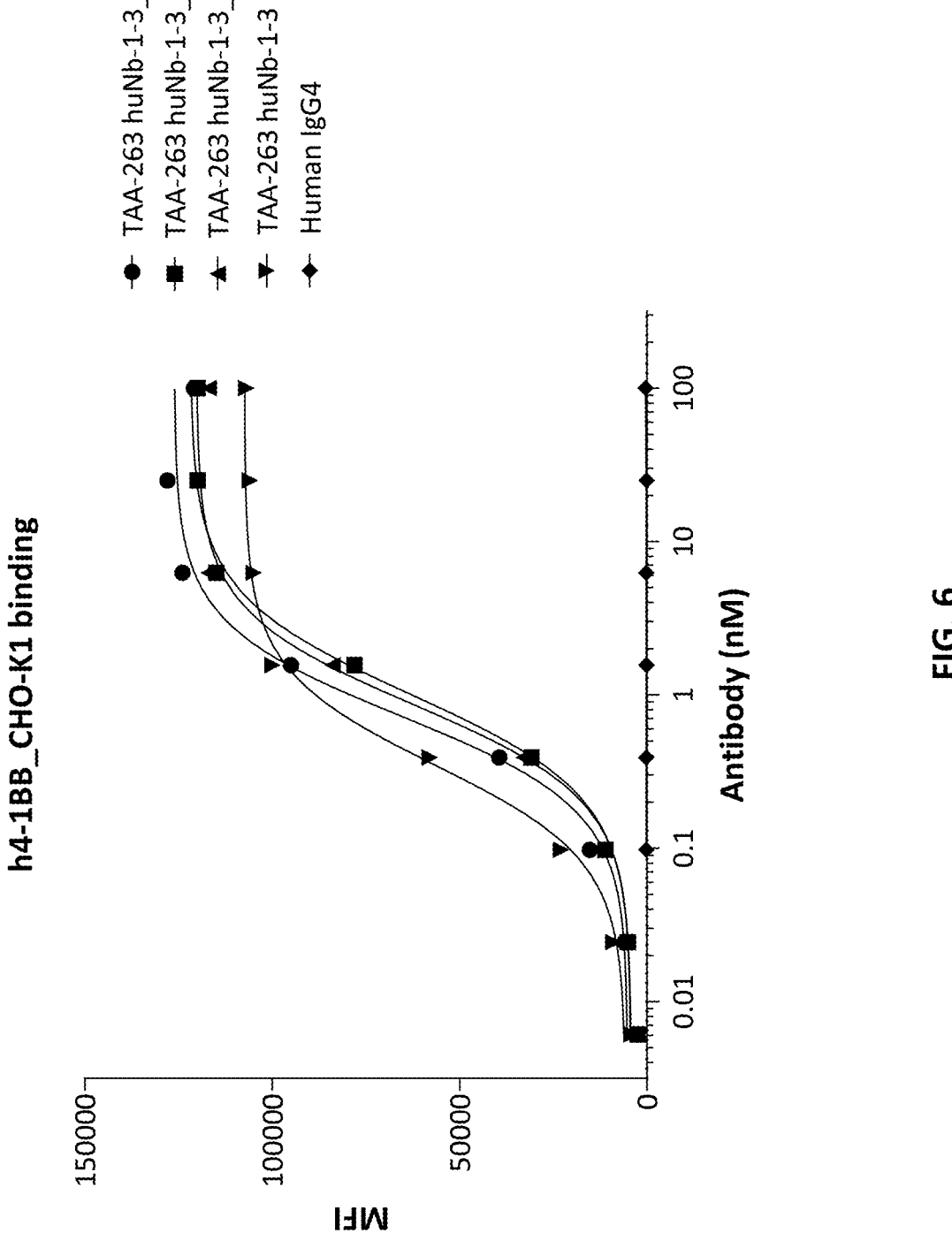
FIG. 6 shows that the optimized anti-4-1BB sequences maintained the comparable binding activity to 4-1BB-bearing CHO-K1 cells as the parental sequence.

The optimized 4-1BB nanobodies-based bispecific antibodies were analyzed for their binding to 4-1BB overexpressed on CHO-K1 cells according to the protocol described above. As shown in FIG. 6, the optimized anti-4-1BB sequences maintained comparable binding activity to 4-1BB-bearing CHO-K1 cells as the parental sequence.

TAA-Dependent 4-1BB Activation

To evaluate the ability of anti-TAA-4-1BB bispecific antibody to activate the 4-1BB signaling, a classical reporter gene assay was used. In this assay, the engineered Jurkat cells which stably express 4-1BB and have an NK-kB luciferase reporter construct integrated into the genome were used as effector cells. CHO-K1 cells engineered to overexpress TAA or the blank CHO-K1 cells were used as target cells. These two types of cells were co-incubated overnight with different concentrations antibodies at 37° C. in 5% CO2 incubator. Then, the substrate of luciferase was added, and the luminescence intensity was determined by a microplate reader.

Figure 7:
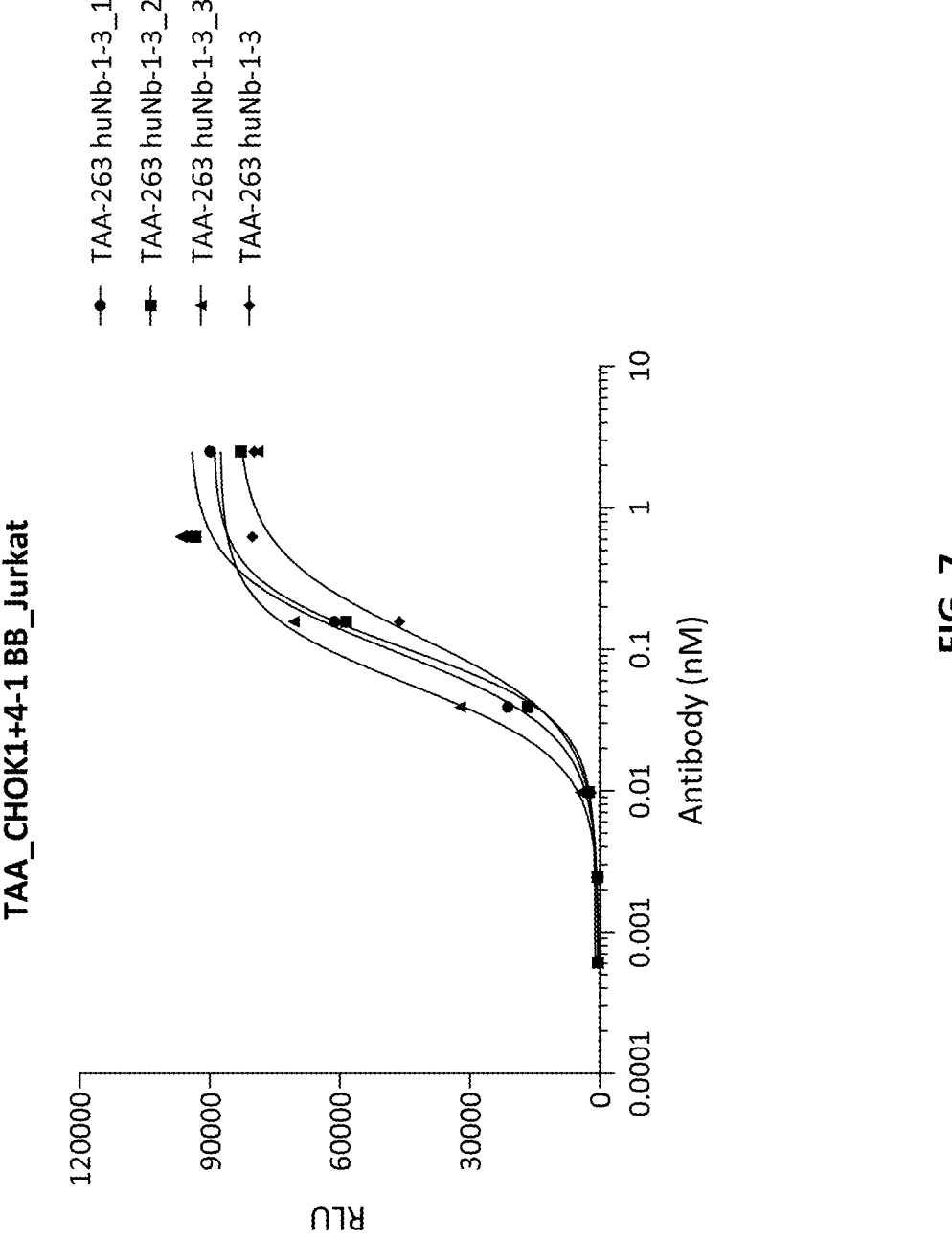
FIG. 7 shows that the optimized anti-4-1BB based bi-specific antibodies had comparable potency in induction of 4-1BB activation in the presence of target cells as the parental antibody TAA-263-1-3.

As shown in FIG. 7, the optimized anti-4-1BB based bi-specific antibodies had comparable potency in induction of 4-1BB activation in the presence of target cells as the parental antibody TAA-263-1-3.

Thermal Stability Assessment

A forced degradation test was conducted to assess the thermal stability of TAA-4-1BB bispecific antibodies. The antibodies were incubated in the buffer containing 20 mM His, 6% Sucrose+0.02% PS80 pH6.0, at 40° C. for 2 weeks. Representative quality attributes especially aggregation and fragmentation were monitored at 2 weeks using SEC-HPLC. Bispecific antibody derived from the parental anti-4-1BB sequence exhibited poor thermal stability as evidenced by aggregation and fragmentation during incubation. In contrast, optimized 4-1BB sequence-based new TAA-4-1BB bispecific antibodies showed acceptable thermal stability at 40° C. for 2 weeks, indicating potential reasonable developability to move forward (Table 9).

TABLE 9

SEC-HPLC characterization of TAA-4-1BB bispecific antibody in forced degradation test

| Sample | Condition | Conc. (mg/ml) | SEC (%) | | |
|---|---|---|---|---|---|
| | | | LMW (%) | Main (%) | HMW (%) |
| TAA-263-1-3_1 | T0 | 6.26 | 1.66 | 97.56 | 0.78 |
| | 40° C. 2 W | 5.88 | 1.59 | 96.15 | 2.26 |
| TAA-263-1-3_2 | T0 | 6.68 | 1.1 | 98.08 | 0.83 |
| | 40° C. 2 W | 5.26 | 1.19 | 96.69 | 2.12 |
| TAA-263-1-3_3 | T0 | 7.13 | 1.89 | 97.25 | 0.85 |
| | 40° C. 2 W | 5.67 | 1.78 | 96.15 | 2.07 |

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

SEQUENCE LISTING

```
Sequence total quantity: 62
SEQ ID NO: 1                moltype = AA  length = 122
FEATURE                     Location/Qualifiers
source                      1..122
                            mol_type = protein
                            organism = Synthetic construct
SEQUENCE: 1
EVDLVESGGG LVQPGGSLRL SCAASGFTFS RSAMSWARQA PGKGFEWVSG IYSGGSTYYV  60
DSVEGRFTIS RDNAKNTVYL QMNSLKPEDT AVYYCATWGS QQIGVWHEDD YWGQGTQVTV  120
SS                                                                122

SEQ ID NO: 2                moltype = AA  length = 122
FEATURE                     Location/Qualifiers
source                      1..122
                            mol_type = protein
                            organism = Synthetic construct
SEQUENCE: 2
EVQLVESGGG LVQPGGSLRL SCAASGFTFS SSAMSWARQT PGKGFEWVSG IYSDGSTYYT  60
DSVKDRFTIS RDNAKNTVYL QMNSLKPEDT AVYYCATWGT LRFGVWAEYD HWGQGTQVTV  120
SS                                                                122

SEQ ID NO: 3                moltype = AA  length = 122
FEATURE                     Location/Qualifiers
source                      1..122
                            mol_type = protein
                            organism = Synthetic construct
SEQUENCE: 3
QVQLVESGGG LVQPGGSLRL SCAASGFTFS SSAMSWARQA PGKDFEWVSY IYSDGNTYYA  60
DSVKGRFTIS RDNAKNTVYL QMNSLKPEDT AVYYCATWHT LRVGVWDEYD YWGQGTQVTV  120
SS                                                                122

SEQ ID NO: 4                moltype = AA  length = 122
FEATURE                     Location/Qualifiers
source                      1..122
                            mol_type = protein
                            organism = Synthetic construct
SEQUENCE: 4
QLQLVESGGG LVQPGGSLRL SCAASGFTFS SSAMSWARQA PGKEFEWVSY IYSDGNTYYT  60
DSVKGRFTVS RDNAKNTVYL QMNSLKPEDT AVYYCATWNS LQVGVWDEYD YWGQGTQVTV  120
SS                                                                122

SEQ ID NO: 5                moltype = AA  length = 122
FEATURE                     Location/Qualifiers
source                      1..122
                            mol_type = protein
                            organism = Synthetic construct
SEQUENCE: 5
EVQLVESGGG LVQPGGSLRL SCAASGFTFS SSAMSWARQV PGKGFEWVAY IYSDGSTYYA  60
DSVKGRFTIS RDNAKDTVYL HMNSLKFEDM AVYYCATWRS QQVGRWDEYD HWGQGTQVTV  120
SS                                                                122
```

-continued

```
SEQ ID NO: 6               moltype = AA  length = 122
FEATURE                    Location/Qualifiers
source                     1..122
                           mol_type = protein
                           organism = Synthetic construct
SEQUENCE: 6
AVQLVESGGG LVQPGGSLRL SCAASGFTFS SYAMSWARQV PGKGFEWVAY IYSDGSTYYA    60
DSVKGRFTIS RDNAKDTVYL HMNSLKFEDM AVYYCATWRS QQVGRWDEYD HWGQGTQVTV   120
SS                                                                 122

SEQ ID NO: 7               moltype = AA  length = 122
FEATURE                    Location/Qualifiers
source                     1..122
                           mol_type = protein
                           organism = Synthetic construct
SEQUENCE: 7
AVQLVESGGG LVQRGGSLKL SCVGSGFDFS DHAMSWARQV PGKGFEWVAY IYSDGSTYYA    60
DSVKGRFTIS RDNAKDTVYL HMNSLKFEDM AVYYCATWRS QQVGRWDEYD HWGQGTQVTV   120
SS                                                                 122

SEQ ID NO: 8               moltype = AA  length = 122
FEATURE                    Location/Qualifiers
source                     1..122
                           mol_type = protein
                           organism = Synthetic construct
SEQUENCE: 8
EVDLVESGGG LVQPGGSLRL SCAASGFTFR SYAMSWARQV PGKGFEWVAY IYSDGSTYYA    60
DSVKGRFTIS RDNAKDTVYL HMNSLKFEDM AVYYCATWRS QQVGRWDEYD HWGQGTQVTV   120
SS                                                                 122

SEQ ID NO: 9               moltype = AA  length = 121
FEATURE                    Location/Qualifiers
source                     1..121
                           mol_type = protein
                           organism = Synthetic construct
SEQUENCE: 9
QLQLVESGGG LVQPGGSLRL SCAASGFALD YSAIGWFRQA PGKEREGVLC ISSSGDVTIY    60
ADSVKGRFTI SRDNAKNTVY LQMNSLKPED TAVYYCVAPR ICSTYSSDDY WGQGTQVTVS   120
S                                                                  121

SEQ ID NO: 10              moltype = AA  length = 121
FEATURE                    Location/Qualifiers
source                     1..121
                           mol_type = protein
                           organism = Synthetic construct
SEQUENCE: 10
QLQLVESGGG LVQPGGSLRL SCAASGFTLA DYAIGWFRQA PGKEREGVLC ISSSGDVTIY    60
ADSVKGRFTI SRDNAKNTVY LQMNSLKPED TAVYYCVAPR ICSTYSSDDY WGQGTQVTVS   120
S                                                                  121

SEQ ID NO: 11              moltype = AA  length = 121
FEATURE                    Location/Qualifiers
source                     1..121
                           mol_type = protein
                           organism = Synthetic construct
SEQUENCE: 11
QVQLVESGGG LVQAGGALRL SCAASGFTLD YSAIGWFRQA PGKEREGVLC ISSSGDVTIY    60
ADSVKGRFTI SRDNAKNTVY LQMNSLKPED TAVYYCVAPR ICSTYSSDDY WGQGTQVTVS   120
S                                                                  121

SEQ ID NO: 12              moltype = AA  length = 121
FEATURE                    Location/Qualifiers
source                     1..121
                           mol_type = protein
                           organism = Synthetic construct
SEQUENCE: 12
EVQVVESGGG LVQPGGSLRL SCAASGSSLD YSAIGWFRQA PGKEREGVLC ISSSGDVTIY    60
ADSVKGRFTI SRDNAKNTVY LQMNSLKPED TAVYYCVAPR ICSTYSSDDY WGQGTQVTVS   120
S                                                                  121

SEQ ID NO: 13              moltype = AA  length = 122
FEATURE                    Location/Qualifiers
source                     1..122
                           mol_type = protein
                           organism = Synthetic construct
SEQUENCE: 13
QVQLVESGGG LVQPGGSLRL SCAASGFTFS SYAMSWARQA PGKDFEWVSY IYSDGNTYYA    60
DSVKGRFTIS RDNAKNTVYL QMNSLKPEDT AVYYCATWHT LRVGVWDEYD YWGQGTQVTV   120
SS                                                                 122
```

-continued

```
SEQ ID NO: 14            moltype = AA  length = 122
FEATURE                  Location/Qualifiers
source                   1..122
                         mol_type = protein
                         organism = Synthetic construct
SEQUENCE: 14
EVQLVESGGG LVQPGGSLRL SCAASGFTFS SSAMSWARQV PGKGFEWVAY IYSDGSTYYA   60
DSVKGRFTIS RDNAKDTVYL HMNSLKFEDM AVYYCATWRS QQVGRWDEYD YWGQGIQVTV  120
SS                                                                 122

SEQ ID NO: 15            moltype = AA  length = 122
FEATURE                  Location/Qualifiers
source                   1..122
                         mol_type = protein
                         organism = Synthetic construct
SEQUENCE: 15
EVDLVESGGG LVQPGGSLRL SCAVSGFTFS NSAMSWARQA PGKEFEWVSS IYSDGKTYYV   60
DSVKGRFTIS RDNAKNTVYL QMSSLKPEDT AVYYCATWKT LRVGVWDESD YWGQGTQVTV  120
SS                                                                 122

SEQ ID NO: 16            moltype = AA  length = 122
FEATURE                  Location/Qualifiers
source                   1..122
                         mol_type = protein
                         organism = Synthetic construct
SEQUENCE: 16
EVQLVESGGG LVQPGGSLMI SCAASGFTFS SSAMSWARQV PGKGFEWVAY IYSDGSTYYA   60
DSVKGRFTIS RDNAKDTVYL HMNSLKFEDM AVYYCATWRS QQVGRWDKYD YWGQGTQVTV  120
SS                                                                 122

SEQ ID NO: 17            moltype = AA  length = 5
FEATURE                  Location/Qualifiers
source                   1..5
                         mol_type = protein
                         organism = Synthetic construct
SEQUENCE: 17
RSAMS                                                                5

SEQ ID NO: 18            moltype = AA  length = 5
FEATURE                  Location/Qualifiers
source                   1..5
                         mol_type = protein
                         organism = Synthetic construct
SEQUENCE: 18
SSAMS                                                                5

SEQ ID NO: 19            moltype = AA  length = 5
FEATURE                  Location/Qualifiers
source                   1..5
                         mol_type = protein
                         organism = Synthetic construct
SEQUENCE: 19
SYAMS                                                                5

SEQ ID NO: 20            moltype = AA  length = 5
FEATURE                  Location/Qualifiers
source                   1..5
                         mol_type = protein
                         organism = Synthetic construct
SEQUENCE: 20
DHAMS                                                                5

SEQ ID NO: 21            moltype = AA  length = 5
FEATURE                  Location/Qualifiers
source                   1..5
                         mol_type = protein
                         organism = Synthetic construct
SEQUENCE: 21
YSAIG                                                                5

SEQ ID NO: 22            moltype = AA  length = 5
FEATURE                  Location/Qualifiers
source                   1..5
                         mol_type = protein
                         organism = Synthetic construct
SEQUENCE: 22
DYAIG                                                                5
```

```
SEQ ID NO: 23            moltype = AA   length = 5
FEATURE                  Location/Qualifiers
source                   1..5
                         mol_type = protein
                         organism = Synthetic construct
SEQUENCE: 23
NSAMS                                                              5

SEQ ID NO: 24            moltype = AA   length = 16
FEATURE                  Location/Qualifiers
source                   1..16
                         mol_type = protein
                         organism = Synthetic construct
SEQUENCE: 24
GIYSGGSTYY VDSVEG                                                 16

SEQ ID NO: 25            moltype = AA   length = 16
FEATURE                  Location/Qualifiers
source                   1..16
                         mol_type = protein
                         organism = Synthetic construct
SEQUENCE: 25
GIYSDGSTYY TDSVKD                                                 16

SEQ ID NO: 26            moltype = AA   length = 16
FEATURE                  Location/Qualifiers
source                   1..16
                         mol_type = protein
                         organism = Synthetic construct
SEQUENCE: 26
YIYSDGNTYY ADSVKG                                                 16

SEQ ID NO: 27            moltype = AA   length = 16
FEATURE                  Location/Qualifiers
source                   1..16
                         mol_type = protein
                         organism = Synthetic construct
SEQUENCE: 27
YIYSDGNTYY TDSVKG                                                 16

SEQ ID NO: 28            moltype = AA   length = 16
FEATURE                  Location/Qualifiers
source                   1..16
                         mol_type = protein
                         organism = Synthetic construct
SEQUENCE: 28
YIYSDGSTYY ADSVKG                                                 16

SEQ ID NO: 29            moltype = AA   length = 17
FEATURE                  Location/Qualifiers
source                   1..17
                         mol_type = protein
                         organism = Synthetic construct
SEQUENCE: 29
CISSSGDVTI YADSVKG                                                17

SEQ ID NO: 30            moltype = AA   length = 16
FEATURE                  Location/Qualifiers
source                   1..16
                         mol_type = protein
                         organism = Synthetic construct
SEQUENCE: 30
SIYSDGKTYY VDSVKG                                                 16

SEQ ID NO: 31            moltype = AA   length = 14
FEATURE                  Location/Qualifiers
source                   1..14
                         mol_type = protein
                         organism = Synthetic construct
SEQUENCE: 31
WGSQQIGVWH EDDY                                                   14

SEQ ID NO: 32            moltype = AA   length = 14
FEATURE                  Location/Qualifiers
source                   1..14
                         mol_type = protein
                         organism = Synthetic construct
SEQUENCE: 32
WGTLRFGVWA EYDH                                                   14
```

-continued

```
SEQ ID NO: 33            moltype = AA  length = 14
FEATURE                  Location/Qualifiers
source                   1..14
                         mol_type = protein
                         organism = Synthetic construct
SEQUENCE: 33
WHTLRVGVWD EYDY                                                      14

SEQ ID NO: 34            moltype = AA  length = 14
FEATURE                  Location/Qualifiers
source                   1..14
                         mol_type = protein
                         organism = Synthetic construct
SEQUENCE: 34
WNSLQVGVWD EYDY                                                      14

SEQ ID NO: 35            moltype = AA  length = 14
FEATURE                  Location/Qualifiers
source                   1..14
                         mol_type = protein
                         organism = Synthetic construct
SEQUENCE: 35
WRSQQVGRWD EYDH                                                      14

SEQ ID NO: 36            moltype = AA  length = 12
FEATURE                  Location/Qualifiers
source                   1..12
                         mol_type = protein
                         organism = Synthetic construct
SEQUENCE: 36
PRICSTYSSD DY                                                        12

SEQ ID NO: 37            moltype = AA  length = 14
FEATURE                  Location/Qualifiers
source                   1..14
                         mol_type = protein
                         organism = Synthetic construct
SEQUENCE: 37
WRSQQVGRWD EYDY                                                      14

SEQ ID NO: 38            moltype = AA  length = 14
FEATURE                  Location/Qualifiers
source                   1..14
                         mol_type = protein
                         organism = Synthetic construct
SEQUENCE: 38
WKTLRVGVWD ESDY                                                      14

SEQ ID NO: 39            moltype = AA  length = 14
FEATURE                  Location/Qualifiers
source                   1..14
                         mol_type = protein
                         organism = Synthetic construct
SEQUENCE: 39
WRSQQVGRWD KYDY                                                      14

SEQ ID NO: 40            moltype = AA  length = 122
FEATURE                  Location/Qualifiers
source                   1..122
                         mol_type = protein
                         organism = Synthetic construct
SEQUENCE: 40
EVQLLESGGG LVQPGGSLRL SCAASGFTFS SSAMSWARQA PGKGLEWVSG IYSGGSTYYT    60
ESVKDRFTIS RDNSKNTLYL QMNSLRAEDT AVYYCAKWGT LRFGVWAEYD HWGQGTLVTV    120
SS                                                                   122

SEQ ID NO: 41            moltype = AA  length = 122
FEATURE                  Location/Qualifiers
source                   1..122
                         mol_type = protein
                         organism = Synthetic construct
SEQUENCE: 41
EVQLLESGGG LVQPGGSLRL SCAASGFTFS SSAMSWARQA PGKGLEWVSG IYSGGSTYYT    60
ESVKDRFTIS RDNSKNTVYL QMNSLKPEDT AVYYCATWGT LRFGVWAEYD HWGQGTLVTV    120
SS                                                                   122

SEQ ID NO: 42            moltype = AA  length = 122
FEATURE                  Location/Qualifiers
```

```
source                    1..122
                          mol_type = protein
                          organism = Synthetic construct
SEQUENCE: 42
EVQLLESGGG LVQPGGSLRL SCAASGFTFS SSAMSWARQT PGKGFEWVSG IYSGGSTYYT  60
ESVKDRFTIS RDNSKNTVYL QMNSLKPEDT AVYYCATWGT LRFGVWAEYD HWGQGTQVTV  120
SS                                                                 122

SEQ ID NO: 43             moltype = AA  length = 122
FEATURE                   Location/Qualifiers
source                    1..122
                          mol_type = protein
                          organism = Synthetic construct
SEQUENCE: 43
EVQLLESGGG LVQPGGSLRL SCAASGFTFS SSAMSWARQA PGKGFEWVSG IYSGGSTYYT  60
ESVKDRFTIS RDNSKNTLYL QMNSLRAEDT AVYYCAKWGT LRFGVWAEYD HWGQGTLVTV  120
SS                                                                 122

SEQ ID NO: 44             moltype = AA  length = 122
FEATURE                   Location/Qualifiers
source                    1..122
                          mol_type = protein
                          organism = Synthetic construct
SEQUENCE: 44
EVQLVESGGG LVQPGGSLRL SCAASGFTFS SSAMSWARQA PGKGLEWVSG IYSGGSTYYT  60
ESVKDRFTIS RDNAKNTLYL QMNSLRPEDT AVYYCATWGT LRFGVWAEYD HWGQGTLVTV  120
SS                                                                 122

SEQ ID NO: 45             moltype = AA  length = 122
FEATURE                   Location/Qualifiers
source                    1..122
                          mol_type = protein
                          organism = Synthetic construct
SEQUENCE: 45
EVQLVESGGG LVQPGGSLRL SCAASGFTFS SSAMSWARQA PGKGFEWVSG IYSGGSTYYT  60
ESVKDRFTIS RDNAKNTVYL QMNSLKPEDT AVYYCATWGT LRFGVWAEYD HWGQGTLVTV  120
SS                                                                 122

SEQ ID NO: 46             moltype = AA  length = 122
FEATURE                   Location/Qualifiers
source                    1..122
                          mol_type = protein
                          organism = Synthetic construct
SEQUENCE: 46
QVQLVESGGG LVKPGGSLRL SCAASGFTFS SSAMSWARQA PGKGLEWVSG IYSGGSTYYT  60
ESVKDRFTIS RDNAKNSLYL QMNSLRAEDT AVYYCARWGT LRFGVWAEYD HWGQGTLVTV  120
SS                                                                 122

SEQ ID NO: 47             moltype = AA  length = 122
FEATURE                   Location/Qualifiers
source                    1..122
                          mol_type = protein
                          organism = Synthetic construct
SEQUENCE: 47
QVQLVESGGG LVKPGGSLRL SCAASGFTFS SSAMSWARQA PGKGFEWVSG IYSGGSTYYT  60
ESVKDRFTIS RDNAKNSLYL QMNSLRPEDT AVYYCATWGT LRFGVWAEYD HWGQGTQVTV  120
SS                                                                 122

SEQ ID NO: 48             moltype = AA  length = 122
FEATURE                   Location/Qualifiers
source                    1..122
                          mol_type = protein
                          organism = Synthetic construct
SEQUENCE: 48
QVQLVESGGG LVQPGGSLRL SCAASGFTFS SSAMSWARQA PGKGFEWVSG IYSGGSTYYT  60
ESVKDRFTIS RDNAKNSVYL QMNSLKPEDT AVYYCATWGT LRFGVWAEYD HWGQGTQVTV  120
SS                                                                 122

SEQ ID NO: 49             moltype = AA  length = 122
FEATURE                   Location/Qualifiers
source                    1..122
                          mol_type = protein
                          organism = Synthetic construct
SEQUENCE: 49
EVQLLESGGG LVQPGGSLRL SCAASGFTFS SSAMSWARQA PGKGLEWVSS IYSSGKTYYV  60
ESVKGRFTIS RDNSKNTLYL QMNSLRAEDT AVYYCAKWKT LRVGVWDESD YWGQGTLVTV  120
SS                                                                 122

SEQ ID NO: 50             moltype = AA  length = 122
```

-continued

```
FEATURE                  Location/Qualifiers
source                   1..122
                         mol_type = protein
                         organism = Synthetic construct
SEQUENCE: 50
EVQLLESGGG LVQPGGSLRL SCAASGFTFS SSAMSWARQA PGKELEWVSS IYSSGKTYYV    60
ESVKGRFTIS RDNAKNTLYL QMSSLRAEDT AVYYCATWKT LRVGVWDESD YWGQGTLVTV   120
SS                                                                  122

SEQ ID NO: 51            moltype = AA  length = 122
FEATURE                  Location/Qualifiers
source                   1..122
                         mol_type = protein
                         organism = Synthetic construct
SEQUENCE: 51
EVDLVESGGG LVQPGGSLRL SCAVSGFTFS SSAMSWARQA PGKEFEWVSS IYSSGKTYYV    60
ESVKGRFTIS RDNAKNTVYL QMSSLRPEDT AVYYCATWKT LRVGVWDESD YWGQGTLVTV   120
SS                                                                  122

SEQ ID NO: 52            moltype = AA  length = 122
FEATURE                  Location/Qualifiers
source                   1..122
                         mol_type = protein
                         organism = Synthetic construct
SEQUENCE: 52
EVQLVESGGG LIQPGGSLRL SCAASGFTFS SSAMSWARQA PGKGFEWVSS IYSSGKTYYV    60
ESVKGRFTIS RDNSKNTLYL QMNSLRAEDT AVYYCARWKT LRVGVWDESD YWGQGTLVTV   120
SS                                                                  122

SEQ ID NO: 53            moltype = AA  length = 122
FEATURE                  Location/Qualifiers
source                   1..122
                         mol_type = protein
                         organism = Synthetic construct
SEQUENCE: 53
EVQLVESGGG LIQPGGSLRL SCAASGFTFS SSAMSWARQA PGKEFEWVSS IYSSGKTYYV    60
ESVKGRFTIS RDNAKNTLYL QMSSLRAEDT AVYYCATWKT LRVGVWDESD YWGQGTQVTV   120
SS                                                                  122

SEQ ID NO: 54            moltype = AA  length = 122
FEATURE                  Location/Qualifiers
source                   1..122
                         mol_type = protein
                         organism = Synthetic construct
SEQUENCE: 54
EVQLVESGGG LVQPGGSLRL SCAVSGFTFS SSAMSWARQA PGKEFEWVSS IYSSGKTYYV    60
ESVKGRFTIS RDNAKNTVYL QMSSLRPEDT AVYYCATWKT LRVGVWDESD YWGQGTQVTV   120
SS                                                                  122

SEQ ID NO: 55            moltype = AA  length = 122
FEATURE                  Location/Qualifiers
source                   1..122
                         mol_type = protein
                         organism = Synthetic construct
SEQUENCE: 55
EVQLVESGGG LVQPGGSLRL SCAASGFTFS SSAMSWARQA PGKGFEWVAS IYSSGKTYYV    60
ESVKGRFTIS RDNAKNSLYL QMNSLRAEDT AVYYCARWKT LRVGVWDESD YWGQGTLVTV   120
SS                                                                  122

SEQ ID NO: 56            moltype = AA  length = 122
FEATURE                  Location/Qualifiers
source                   1..122
                         mol_type = protein
                         organism = Synthetic construct
SEQUENCE: 56
EVQLVESGGG LVQPGGSLRL SCAASGFTFS SSAMSWARQA PGKGFEWVSS IYSSGKTYYV    60
ESVKGRFTIS RDNAKNSLYL QMSSLRAEDT AVYYCATWKT LRVGVWDESD YWGQGTLVTV   120
SS                                                                  122

SEQ ID NO: 57            moltype = AA  length = 122
FEATURE                  Location/Qualifiers
source                   1..122
                         mol_type = protein
                         organism = Synthetic construct
SEQUENCE: 57
EVQLVESGGG LVQPGGSLRL SCAVSGFTFS SSAMSWARQA PGKEFEWVSS IYSSGKTYYV    60
ESVKGRFTIS RDNAKNSVYL QMSSLRPEDT AVYYCATWKT LRVGVWDESD YWGQGTLVTV   120
SS                                                                  122
```

US 12,692,318 B2

```
SEQ ID NO: 58          moltype = AA  length = 16
FEATURE                Location/Qualifiers
source                 1..16
                       mol_type = protein
                       organism = Synthetic construct
SEQUENCE: 58
GIYSGGSTYY TESVKD                                                  16

SEQ ID NO: 59          moltype = AA  length = 16
FEATURE                Location/Qualifiers
source                 1..16
                       mol_type = protein
                       organism = Synthetic construct
SEQUENCE: 59
SIYSSGKTYY VESVKG                                                  16

SEQ ID NO: 60          moltype = AA  length = 122
FEATURE                Location/Qualifiers
source                 1..122
                       mol_type = protein
                       organism = Synthetic construct
SEQUENCE: 60
EVQLVESGGG LVQPGGSLRL SCAASGFTFS SSAMSWARQA PGKGFEWVSG IYSGGSTYYT  60
ESVKDRFTIS RDNSKNTVYL QMNSLKPEDT AVYYCATWGT LRFGVWAEYD HWGQGTQVTV  120
SS                                                                122

SEQ ID NO: 61          moltype = AA  length = 122
FEATURE                Location/Qualifiers
source                 1..122
                       mol_type = protein
                       organism = Synthetic construct
SEQUENCE: 61
EVQLVESGGG LVQPGGSLRL SCAASGFTFS SSAMSWARQA PGKGFEWVSG IYSGGSTYYT  60
ESVKDRFTIS RDNAKNTVYL QMNSLKPEDT AVYYCATWGT LRFGVWAEYD HWGQGTLVTV  120
SS                                                                122

SEQ ID NO: 62          moltype = AA  length = 122
FEATURE                Location/Qualifiers
source                 1..122
                       mol_type = protein
                       organism = Synthetic construct
SEQUENCE: 62
EVQLVESGGG LVQPGGSLRL SCAASGFTFS SSAMSWARQT PGKGFEWVSG IYSGGSTYYT  60
ESVKDRFTIS RDNSKNTLYL QMNSLRPEDT AVYYCATWGT LRFGVWAEYD HWGQGTQVTV  120
SS                                                                122
```

What is claimed is:

1. A single domain antibody or a polypeptide comprising the single domain antibody, wherein the single domain antibody has binding specificity to the human 4-1BB protein and comprises a complementarity determining region 1 (CDR1), a CDR2 and a CDR3, wherein the CDR1 comprises the amino acid sequence of SEQ ID NO:18, the CDR2 comprises the amino acid sequence of SEQ ID NO:58, and the CDR3 comprises the amino acid sequence of SEQ ID NO: 32.

2. The antibody or polypeptide of claim 1, which comprises the amino acid sequence of any one of SEQ ID NO:40-48 and 60-62.

3. The antibody or polypeptide of claim 1, which comprises the amino acid sequence of SEQ ID NO: 60.

4. The antibody or polypeptide of claim 1, wherein the polypeptide is a chimeric antigen receptor (CAR) or a bispecific antibody having a binding specificity to an antigen different from 4-1BB.

5. A bispecific antibody comprising the antibody of claim 1 and a second antibody or antigen-binding fragment having binding specificity to a target antigen that is not 4-1BB.

6. A composition comprising the antibody or polypeptide of claim 1 and a pharmaceutically acceptable carrier.

* * * * *